US012682993B2

(12) United States Patent
Li et al.

(10) Patent No.: US 12,682,993 B2
(45) Date of Patent: Jul. 14, 2026

(54) ENHANCED RECORDING OF RESCUE EVENTS

(71) Applicant: Stryker Corporation, Kalamazoo, MI (US)

(72) Inventors: Hanqiu Li, Seattle, WA (US); Tara Fleishauer, Napa, CA (US); Mark G. Killebrew, San Clemente, CA (US); Steven Barry Duke, Bothell, WA (US); Shalini Majumdar, Covington, WA (US)

(73) Assignee: Stryker Corporation, Portage, MI (US)

( * ) Notice: Subject to any disclaimer, the term of this patent is extended or adjusted under 35 U.S.C. 154(b) by 72 days.

(21) Appl. No.: 18/415,017

(22) Filed: Jan. 17, 2024

(65) Prior Publication Data

US 2024/0242798 A1     Jul. 18, 2024

Related U.S. Application Data

(60) Provisional application No. 63/439,533, filed on Jan. 17, 2023.

(51) Int. Cl.
| | |
|---|---|
| *G16H 10/60* | (2018.01) |
| *A61B 90/98* | (2016.01) |
| *G16H 30/40* | (2018.01) |
| *G16H 40/40* | (2018.01) |

(52) U.S. Cl.
CPC ............. *G16H 10/60* (2018.01); *A61B 90/98* (2016.02); *G16H 30/40* (2018.01); *G16H 40/40* (2018.01)

(58) Field of Classification Search
None
See application file for complete search history.

(56) References Cited

U.S. PATENT DOCUMENTS

| | | | | |
|---|---|---|---|---|
| 9,035,787 B2 * | 5/2015 | Bongberg | .............. | H04M 11/04 |
| | | | | 340/815.45 |
| 9,218,455 B2 | 12/2015 | Neff | | |
| 10,341,866 B1 | 7/2019 | Spencer et al. | | |
| 11,213,689 B2 * | 1/2022 | Freeman | ................ | A61B 5/316 |
| 11,344,202 B2 | 5/2022 | Freeman et al. | | |
| 11,924,282 B2 * | 3/2024 | Durrant | ................. | H04L 67/125 |
| 12,144,584 B2 * | 11/2024 | Freeman | .............. | A61B 5/0077 |
| 12,512,190 B2 * | 12/2025 | Ashmore | .............. | A61B 5/7275 |

(Continued)

FOREIGN PATENT DOCUMENTS

AU          2021245840 A1      9/2022

OTHER PUBLICATIONS

Extended European Search Report for EP Patent Application No. 24152374.5, dated Jun. 5, 2024, 8 pages.

(Continued)

*Primary Examiner* — Jonathan Ng
(74) *Attorney, Agent, or Firm* — Lee & Hayes, P.C.

(57) ABSTRACT

Techniques for generating and updating electronic records of rescue events are described. In a rescue scene, a medical device monitors and/or treats a patient. An example tracking device determines an identifier of the medical device by analyzing a signal corresponding to a medical device. In addition, the tracking device identifies a physiological parameter of the patient. The tracking device generates an electronic record of the patient that includes the identifier and the physiological parameter. The tracking device further outputs the electronic record.

15 Claims, 8 Drawing Sheets

(56) References Cited

U.S. PATENT DOCUMENTS

| | | | |
|---|---|---|---|
| 2004/0172070 A1* | 9/2004 | Moore | G16H 10/20 607/5 |
| 2011/0305376 A1* | 12/2011 | Neff | G16H 40/20 382/128 |
| 2014/0233788 A1* | 8/2014 | Fox | G16H 40/67 382/103 |
| 2014/0275876 A1 | 9/2014 | Hansen et al. | |
| 2016/0375261 A1* | 12/2016 | Galvin | A61N 1/3925 607/5 |
| 2019/0362841 A1* | 11/2019 | Aysin | G06F 8/65 |
| 2019/0381307 A1 | 12/2019 | Hoss et al. | |
| 2020/0312340 A1 | 10/2020 | Hudson | |
| 2021/0304881 A1* | 9/2021 | White | G06K 7/1413 |
| 2022/0072321 A1* | 3/2022 | O'Connor | G16H 15/00 |
| 2023/0019463 A1* | 1/2023 | Duke | G16H 15/00 |
| 2024/0282421 A1* | 8/2024 | Webster | A61N 1/3904 |

OTHER PUBLICATIONS

Ronneberger, et al., "U-Net: Convolutional Networks for Biomedical Image Segmentation," MICCAI 2015, May 2015, pp. 234-241.

* cited by examiner

PATIENT RECORD
400

PHYSIOLOGICAL
PARAMETER(S)
402

TREATMENT
PARAMETER(S)
404

LOCATION
INDICATOR
406

TIME INDICATOR
408

PATIENT
IDENTIFIER
410

DEVICE
IDENTIFIER
412

500

Device A

TAG
INFORMATION
506

TAG
502

TRACKING
DEVICE 504

700

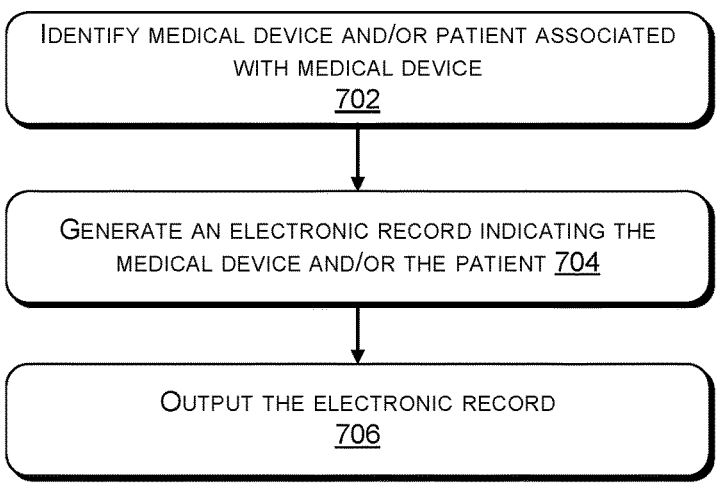

IDENTIFY MEDICAL DEVICE AND/OR PATIENT ASSOCIATED WITH MEDICAL DEVICE
702

GENERATE AN ELECTRONIC RECORD INDICATING THE MEDICAL DEVICE AND/OR THE PATIENT 704

OUTPUT THE ELECTRONIC RECORD
706

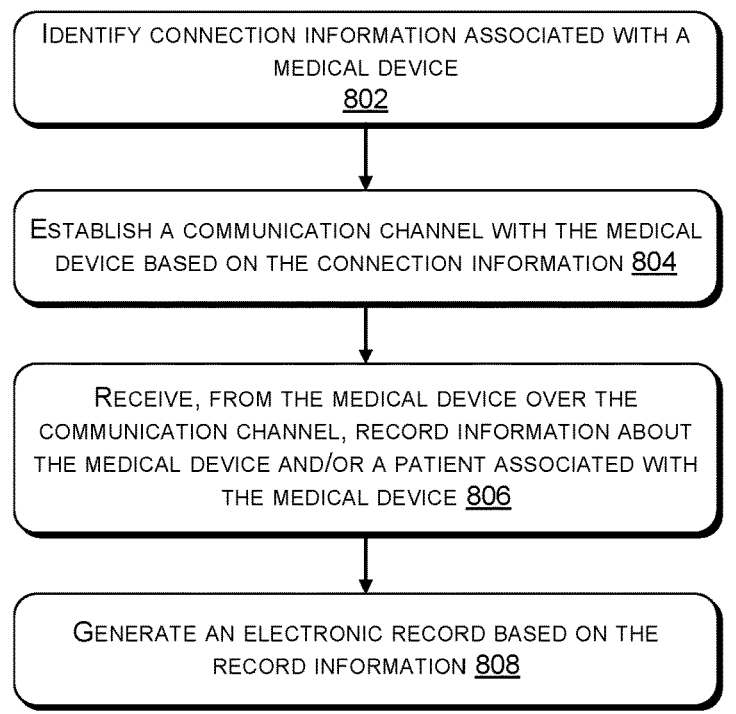

IDENTIFY CONNECTION INFORMATION ASSOCIATED WITH A MEDICAL DEVICE
802

ESTABLISH A COMMUNICATION CHANNEL WITH THE MEDICAL DEVICE BASED ON THE CONNECTION INFORMATION 804

RECEIVE, FROM THE MEDICAL DEVICE OVER THE COMMUNICATION CHANNEL, RECORD INFORMATION ABOUT THE MEDICAL DEVICE AND/OR A PATIENT ASSOCIATED WITH THE MEDICAL DEVICE 806

GENERATE AN ELECTRONIC RECORD BASED ON THE RECORD INFORMATION 808

FIG. 8

ENHANCED RECORDING OF RESCUE EVENTS

CROSS-REFERENCE TO RELATED APPLICATION

This application claims priority to U.S. Provisional App. No. 63/439,533, which was filed on Jan. 17, 2023, and is incorporated by reference herein in its entirety.

BACKGROUND

Various types of medical devices are designed to monitor and/or treat patients. For example, a medical device may include a sensor configured to detect a signal indicative of a patient's condition. In some examples, the medical device is further configured to treat a pathological condition of a patient. For instance, certain external defibrillators are configured to detect an electrocardiogram (ECG) of a patient, determine whether the ECG is indicative of ventricular fibrillation (VF), and treat the VF by administering an electrical shock to the patient.

In some emergency circumstances, medical devices are utilized outside of a clinical environment. For example, if the patient collapses in an airport terminal, then the defibrillator may be utilized in the airport terminal. However, in many cases, patients are later transported into a formal, clinical environment. For instance, the patient may be transported to a hospital after being stabilized in the airport terminal.

BRIEF DESCRIPTION OF THE DRAWINGS

FIG. 7 illustrates an example process for generating an electronic record.

FIG. 8 illustrates an example process for generating an electronic record based on communication with a medical device.

DETAILED DESCRIPTION

Various implementations described herein relate to enhanced techniques for tracking rescue events in which a medical device is utilized to monitor and/or treat a patient.

In some cases, vital context to a patient's condition is gathered by or otherwise associated with a medical device that is utilized outside of a clinical environment. The context, for example, includes whether or not the medical device is utilized, the type of medical device, data detected by the medical device, a condition of the patient detected by the medical device, where the medical device was located, or information about a treatment administered by the medical device. This context may be relevant to future clinical decisions about how to monitor or treat the patient. However, the medical device may be incapable of directly communicating information indicating the context to another clinical device utilized by a care provider that later manages monitoring or treatment of the patient. In some cases, this discontinuity of information can reduce the quality of the care that the patient later receives. In some cases, this discontinuity can endanger the patient in the clinical environment.

Various implementations of the present disclosure address these and other problems by providing techniques for obtaining and communicating the context to subsequent providers. According to some examples, a tracking device is configured to generate an electronic record indicating a rescue event in which a patient is being monitored or treated by a medical device, which may be different than the tracking device. In some cases, the tracking device elucidates information relevant to the patient or the medical device. For instance, the tracking device detects a signal from the medical device and analyzes the signal to infer information related to the rescue event. According to some examples, the tracking device obtains the information even if the medical device is incapable of directly communicating with the tracking device. Thus, various implementations described herein can be used with medical devices having various manufacturers and communication capabilities. In some cases, the tracking device communicates with the medical device directly in order to identify the relevant information. The tracking device, for instance, transmits the electronic record to an external device, thereby enabling a care provider to later review the information even if the care provider does not have access to the medical device itself.

Implementations will now be described with reference to the accompanying figures.

Figure 1:
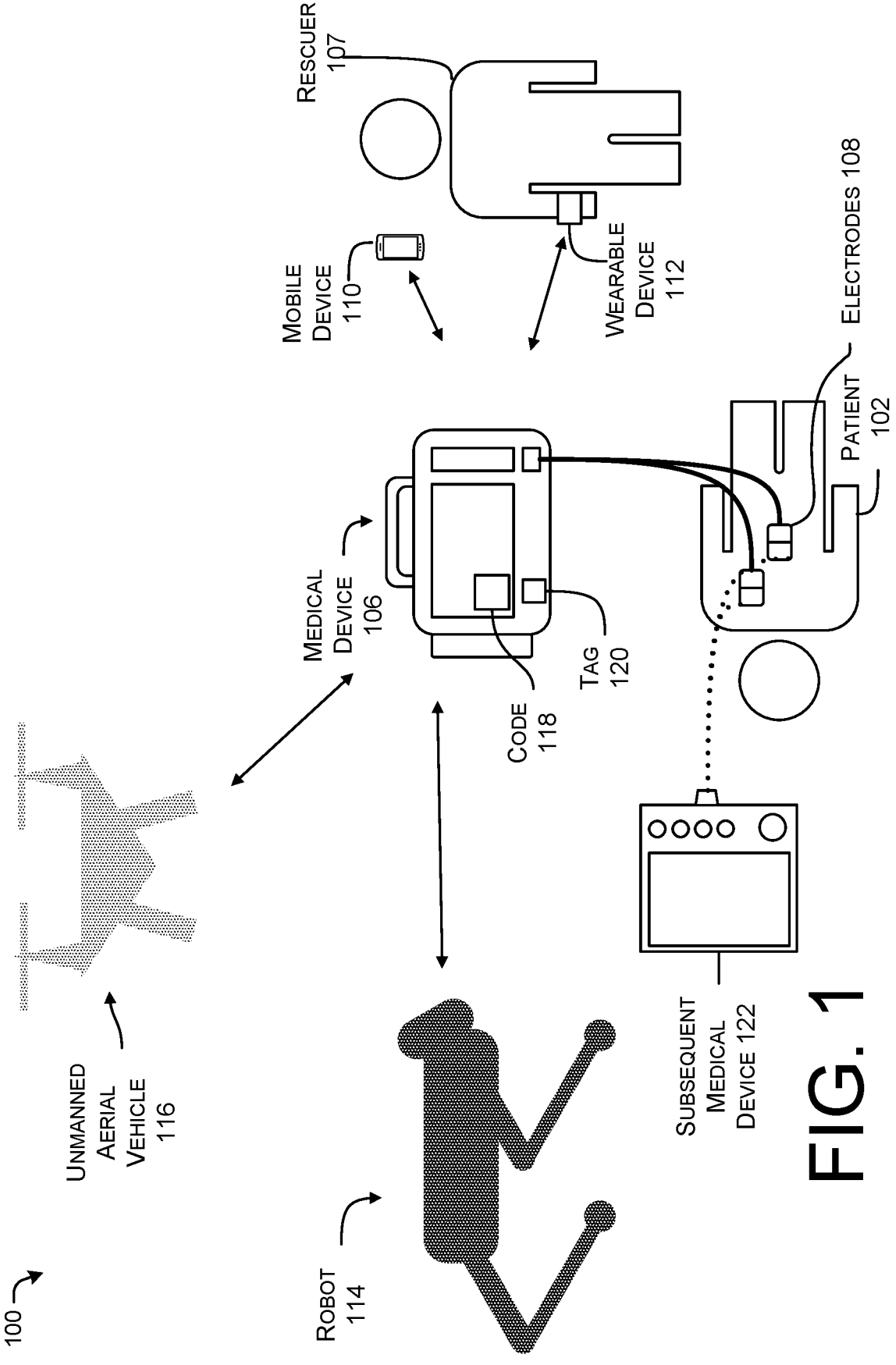
FIG. 1 illustrates an example rescue scene whose details can be recorded in an enhanced electronic record.

FIG. 1 illustrates an example rescue scene 100 whose details can be recorded in an enhanced electronic record. In various implementations, a patient 102 is experiencing an emergency medical condition at the rescue scene 100. In some cases, the patient 102 has collapsed or is otherwise unresponsive. For example, the patient 102 may be experiencing cardiac arrest. In some cases, the patient 102 is exhibiting a disorganized heart rhythm that prevents the heart from adequately perfusing blood to the brain and other vital organs of the patient 102. In some cases, the heart rhythm is a shockable arrhythmia. As used herein, the term "shockable arrhythmia" can refer to a heart rhythm that is treatable by the application of an electric shock to the patient. Examples of shockable arrhythmias include ventricular fibrillation (VF) and pulseless ventricular tachycardia (VT). In some cases, the patient 102 is exhibiting another type of arrhythmia, such as bradycardia or asystole. According to some implementations, the patient 102 is not breathing.

In various cases, a rescuer 104 is available to assist the patient 102. For instance, the rescuer 104 has connected the patient 102 to a medical device 106 that is configured to monitor and/or administer a treatment to the patient 102. In some implementations, the rescuer 104 is a trained care provider, such as an emergency medical technician (EMT). In some cases, the rescuer 104 is an untrained bystander. The medical device 106, for example, may be configured to be operated by an untrained user. According to various implementations, the medical device 106 is a defibrillator (e.g., an automated external defibrillator (AED) or monitor-defibrillator), a mechanical chest compression device, or a ventilation device.

The medical device 106 is configured to detect one or more physiological parameters of the patient 102. As used herein, the term "physiological parameter," and its equivalents, may refer to a signal and/or metric indicative of the signal that corresponds to a clinically relevant state of a subject (e.g., the patient 102). Examples of physiological parameters include blood pressure, blood oxygenation (e.g., a peripheral capillary oxygen saturation (SpO2), regional oxygen saturation (rsO2), or plethysmograph), a capnograph, an end-tidal parameter (e.g., an end tidal CO2) of, a mechanical pulse (e.g., on a wrist), a temperature, a respiration rate, or an electroencephalogram (EEG). The medical device 106 includes one or more sensors configured to detect the physiological parameter(s). For example, the medical device 106 includes electrodes affixed to a chest of the patient 102, a blood pressure cuff, an ultrasound-based blood pressure sensor, a pulse oximeter, a regional oxygen saturation sensor, a capnography sensor (e.g., a nondispersive infrared sensor (NDIR) CO2 sensor), a flow sensor, an oxygen sensor, an accelerometer, a thermometer, a pressure sensor, a moisture sensor, a voltmeter, a current sensor, or any combination thereof.

In some examples, the medical device 106 is connected to one or more accessory devices configured to detect the physiological parameter(s). The accessory device(s), for instance, include at least one sensor configured to detect the physiological parameter(s). For example, the medical device 106 is connected to a set of electrodes 108 affixed to the body of the patient 102. In various cases, the electrodes 108 are affixed to the skin of the patient 102. By detecting a relative voltage between the electrodes 108 over time, the medical device 106 detects an electrocardiogram (ECG) of the patient 102.

According to some cases, the medical device 106 is configured to administer a treatment to the patient 102. In some implementations, the medical device 106 is configured to administer an electrical shock to the heart of the patient 102 via the electrodes 108. In some cases, the electrical shock defibrillates the patient 102. According to some implementations, the medical device 106 is configured to administer pace pulses to the patient 102 via the electrodes 108.

In various implementations of the present disclosure, the rescue scene 100 is outside of a clinical environment. For instance, the rescue scene 100 is outside of a hospital or medical clinic. However, the patient 102 may be subjected to further monitoring and/or treatment in the clinical environment. For example, the patient 102 may be transported to the clinical environment via an ambulance or other transportation mechanism.

In some cases, the patient 102 is disconnected from the medical device 106 when the patient 102 is transferred to the clinical environment. The clinical environment may include other medical devices configured to monitor and/or treat the patient 102. These medical device(s), in some cases, have enhanced functionality over the medical device 106, but may be nonportable.

In particular examples, the medical device 106 may be an AED that is stored in a public area, such as in a cabinet disposed in an airport terminal. The patient 102 may collapse due to hypoxia caused by a shockable arrhythmia. The AED, in some implementations, may defibrillate the patient 102 shortly after the patient 102 collapses in the airport terminal, which can cause the heart of the patient 102 to resume pumping blood effectively, thereby reducing the time at which the brain of the patient 102 is starved of oxygen and reducing the impact of the hypoxia on the brain of the patient 102. Later, a professional EMT team may arrive at the airport terminal and may transport the patient 102 to a hospital for evaluation by a trained clinician and more complex monitoring and treatments. In some cases, the EMT team may temporarily monitor and/or treat the patient 102 in an ambulance using a monitor-defibrillator. At the hospital, a cardiologist may use an inpatient cardiac monitor to monitor the patient 102, and may also utilize a tablet computer (or other computing device) to track the condition of the patient 102. Thus, the care of the patient 102 may be implemented by different people, in different environments, using different devices.

When the patient 102 is transferred to the clinical environment, important context for the status of the patient 102 at the rescue scene 100, as well as treatments performed on the patient 102, may be lost. For example, the medical device 106 may detect that the patient 102 had a shockable arrhythmia, administer an electrical shock via the electrodes 108, and detect that the shockable arrhythmia has been at least temporarily resolved with the electrical shock. If the patient 102 later refibrillates after being transported to a hospital, it may be clinically advantageous to attempt to defibrillate the patient 102 with an electrical shock having the same voltage as the one administered by the medical device 106. However, if the medical device 106 was unable to even temporarily resolve the shockable arrhythmia with the electrical shock administered via the electrodes 108, then it may be clinically advantageous for the patient 102 to be treated with an electrical shock that is administered at a higher voltage than the electrical shock administered by the medical device 106 when the patient 102 arrives at the hospital.

However, the medical device 106 may be unable to transmit or even store a record associated with the patient 102. For example, in some cases, the medical device 106 is unable to transmit patient-related data across a communication network, such as a wireless network and/or the Internet. In some examples, the medical device 106 does not store patient data at all. For example, the medical device 106 may be an early-generation AED without data storage capabilities or wireless communication capabilities.

Furthermore, in various implementations, the medical device 106 may have a different manufacturer than any other device at the rescue scene 100. For example, the medical device 106 may be an AED manufactured by Company A. Company A may manufacture a suite of related emergency medical devices, such as mechanical chest compression devices, ventilation devices, and monitor-defibrillators. In some cases, Company A may enable communication between the types of devices it manufactures, as a way of motivating EMS teams to exclusively purchase Company A devices. However, for the same reason, Company A may prevent the medical device 106 from communicating directly with devices that are not manufactured by Company A. For instance, a monitor-defibrillator manufactured by Company B may be unable to communicate with the medical device 106. Thus, even if the medical device 106 is configured to store patient data and communicate with other devices having the same manufacturer, the medical device 106 may be unable to communicate the patient data in the rescue scene 100.

Due to various communication deficits of the medical device 106, clinicians at the hospital (or other downstream clinical environment) may be unable to access any record indicating the ECG detected by the medical device 106, the electrical shock administered by the medical device 106, or even information indicating that the medical device 106 was capable of administering a defibrillation treatment to the patient 102. The transfer of the patient 102 from the rescue scene to the hospital can cause a significant discontinuity of care that can negatively impact later care of the patient 102. It would therefore be advantageous if data stored by the medical device 106 or other characteristics of the medical device 106 could be communicated to a downstream care provider that later manages treatment of the patient 102.

In various implementations of the present disclosure, an electronic record associated with the patient 102 can be generated and conveyed to a clinician that later cares for the patient 102 at a clinical setting outside of the rescue scene 100. The electronic record, for instance, includes data indicative of an identity of the patient 102, an identity of the medical device 106, the physiological parameter(s) detected by the medical device 106, the treatment administered to the patient 102 by the medical device 106, or any other details associated with the patient 102 and medical device 106 at the rescue scene 100.

According to various examples, a tracking device is configured to generate and/or receive the electronic record associated with the patient 102. In some cases, a tracking device associated with the rescuer 107 generates an electronic record of the patient 102. As used herein, the term "tracking device," and its equivalents, may refer to a computing device configured to detect a signal from a medical device, to store data associated with the signal in an electronic record, to communicate the data to an external device, or any combination thereof. Examples of tracking devices include mobile devices, audio recorders, other medical devices, robotic devices, and so on.

In some cases, the tracking device is associated with the rescuer 107. For example, the rescuer 107 may be associated with a mobile device 110 (e.g., a mobile phone, a tablet computer, or some other type of computing device) that receives and/or generates the electronic record. In some examples, the rescuer 107 is wearing a wearable device 112 that receives and/or generates the electronic record. For example, the wearable device 112 includes a smart watch or a smart glasses device.

In some examples, the tracking device is configured to survey the rescue scene 100. For example, a robot 114 may be present in the rescue scene 100. In some examples, the robot 114 is an ambulatory computing device that is configured to move throughout the rescue scene 100 via multiple robotic legs, wheels, or the like. According to some cases, an unmanned aerial vehicle (UAV) 116 is located in the rescue scene 100. For example, the UAV 116 is a computing device that includes one or more propellers configured to move the UAV 116 throughout the air in the rescue scene 100.

According to some examples, the robot 114 or the UAV 116 includes a camera and/or thermal sensor configured to survey the rescue scene 100. In some cases, the robot 114 or the UAV 116 includes at least one processor configured to cause a movement component of the robot 114 (e.g., the legs of the robot 114) or the UAV 116 (e.g., the propeller of the UAV 116) from one position to another position in the rescue scene 100. For example, the processor(s) is configured to detect an anomaly in a video or heatmap depiction of the rescue scene 100 and move the robot 114 or the UAV 116 to a position wherein the robot 114 or the UAV 116 can more clearly monitor the anomaly. Examples of anomalies include an unconscious person, an injured person, or a dangerous environment (e.g., a downed power line, a fire, a flood, or the like). In various implementations, the robot 114 or the UAV 116 includes a light source (e.g., a light-emitting diode (LED)) configured to illuminate at least a portion of the rescue scene 100. In some examples, the robot 114 or the UAV 116 is configured to illuminate the anomaly.

According to some examples, the robot 114 or UAV 116 may facilitate communication between devices at the rescue scene 100 and remote devices. For instance, the robot 114 or UAV 116 may include a wireless access point (AP), a base station, or other device configured to transmit and/or receive communication signals from devices within the rescue scene 100. The robot 114 or UAV 116 may further be configured to transmit and/or receive data (such as data encoded in the communication signals) with a wide area network (WAN), such as a cellular core network, a satellite network, the Internet, or a combination thereof. Devices of other stakeholders, such as clinicians, may additionally be connected to the WAN. Therefore, the robot 114 or UAV 116 may enable important patient-relevant communications between the rescue scene 100 and clinicians in other environments (e.g., a hospital) in order to enhance patient care and treatment. In some cases, the robot 114 and/or the UAV 116 is stored in an ambulance or among other accessories utilized by the rescuer 107. The rescuer 107, for instance, may initiate deployment of the robot 114 and/or the UAV 116 upon arriving to the rescue scene 100. In some cases, the robot 114 and/or the UAV 116 is deployed automatically, such as based on scene activity, unit call status (e.g., a call status of a unit of an organization including the rescuer 107), or quality of detected wireless coverage (e.g., when the device detects that the rescue scene 100 is out of a coverage area of a wireless AP or base station).

In some cases, the robot 114 or UAV 116 is configured to assist the rescuer 107 with identifying individuals in need of assistance at the rescue scene 100. For example, in some cases, the patient 102 is hidden from view by the rescuer 107 when the rescuer arrives at the rescue scene 100. In various implementations, the robot 114 or UAV 116 is deployed at the rescue scene 100 and configured to automatically survey the rescue scene 100 for visual signs of the patient 102. The robot 114 or UAV 116 may autonomously move throughout the rescue scene 100 and capture images of the rescue scene 100. In some cases, the robot 114 or UAV 116 may move into spaces that are inaccessible to the rescuer 107, or may otherwise capture images from views that are inaccessible to the rescuer 107. For example, the UAV 116 may hover over the rescue scene 100 and capture an image of the patient 102, even if the patient 102 is blocked from view from a terrestrial viewpoint of the rescuer 107 (e.g., by a wall or debris). In some cases, the robot 114 or UAV 116 captures the images using an infrared camera, and can therefore detect the patient 102 in dark environments (e.g., at night). Upon capturing an image of the patient 102, the robot 114 or UAV 116 may output a signal that indicates the patient 102 to the rescuer 107, such as an audible alarm. Upon perceiving the signal indicating the patient 102, the rescuer 107 may be able to assist the patient 102. In some cases, the robot 114 or UAV 116 may identify one or more additional patients in need of assistance at the rescue scene 100.

In various implementations, the tracking device includes a sensor configured to detect a signal associated with the medical device 106. In some cases, the sensor includes a camera configured to capture an image of the medical device 106. In various implementations, the tracking device includes the image of the medical device 106 in the electronic record. Accordingly, a clinician treating the patient 102 at a later time may review the electronic record and be informed that the patient 102 was monitored and/or treated by the medical device 106.

In some cases, the tracking device identifies the medical device 106 by analyzing the image of the medical device 106. For example, by analyzing the image, the tracking device may identify a characteristic of the medical device 106, such as a logo on a surface of the medical device 106, an identification (ID) number of the medical device 106, a shape of the medical device 106, a color of the medical device, or the like. In some cases, the image depicts a code 118 that is displayed by and/or printed on the medical device 106. In some examples, the code 118 is a barcode (e.g., a QR code) that indicates an identifier of the medical device 106. For instance, the code 118 is printed on a label that is attached to the medical device 106, or output by a display (e.g., a screen) of the medical device 106.

To analyze the image, the tracking device may perform one or more image recognition techniques. In some cases, the tracking device stores or otherwise accesses a trained machine learning (ML) model. As used herein, the terms "machine learning," "ML," and their equivalents may refer to type of model that includes parameters that are optimized based on training data, and, once optimized, are configured to identify features, make decisions, or make predictions based on additional data that is outside of the training data. ML models can be trained (i.e., the parameters of the models can be optimized) using supervised, unsupervised, or semi-supervised learning techniques.

In some cases, the ML model includes at least one neural network (NN). The term "Neural Network (NN)," and its equivalents, may refer to a model with multiple hidden layers, wherein the model receives an input (e.g., an image) and transforms the input by performing operations via the hidden layers. An individual hidden layer may include multiple "neurons," each of which may be disconnected from other neurons in the layer. An individual neuron within a particular layer may be connected to multiple (e.g., all) of the neurons in the previous layer. A NN may further include at least one fully connected layer that receives a feature map output by the hidden layers and transforms the feature map into the output of the NN.

As used herein, the term "CNN," and its equivalents, may refer to a type of NN model that performs at least one convolution (or cross correlation) operation on an input image and may generate an output image based on the convolved (or cross-correlated) input image. A CNN may include multiple layers that transforms an input image into an output image via a convolutional or cross-correlative model defined according to one or more parameters. The parameters of a given layer may correspond to one or more filters, which may be digital image filters that can be represented as images. A filter in a layer may correspond to a neuron in the layer. A layer in the CNN may convolve or cross correlate its corresponding filter(s) with the input image in order to generate the output image. In various examples, a neuron in a layer of the CNN may be connected to a subset of neurons in a previous layer of the CNN, such that the neuron may receive an input from the subset of neurons in the previous layer and may output at least a portion of an output image by performing an operation (e.g., a dot product, convolution, cross-correlation, or the like) on the input from the subset of neurons in the previous layer. The subset of neurons in the previous layer may be defined according to a "receptive field" of the neuron, which may also correspond to the filter size of the neuron. U-Net (see, e.g., Ronneberger, et al., arXiv: 1505.04597v1, 2015) is an example of a CNN model.

According to various implementations, the tracking device is configured to identify the medical device 106 by inputting the image of the medical device 106 into a CNN (e.g., a U-Net model) that is trained to identify medical devices. For example, the CNN is trained using training data that includes multiple images of different types of medical devices, from different angles, taken in different lighting conditions, wherein at least one of the medical devices depicted in the training data has the same type as the medical device 106. In some cases, the training data further includes identifiers (e.g., labels) indicating the types of medical devices depicted in the training data. In some cases, the tracking device trains the CNN, and in some cases, the CNN is trained by a different computing device. In various implementations, the input of the CNN is the image of the medical device 106 and the output of the CNN is an identifier of the medical device 106.

In some implementations, the tracking device includes at least one microphone configured to detect a sound from the medical device 106. For example, the tracking device detects an audible alarm output by the medical device 106, a user prompt output by the medical device 106 (e.g., an audible instruction for operating the medical device 106), a power-on sound of the medical device 106, or the sound of a treatment administered by the medical device 106. This sound, for example, can be uniquely associated with a model of the medical device 106. In some implementations, the tracking device detects one or more spectral features of the sound (e.g., a tone that is within the sound) and identifies the medical device based on the spectral feature(s).

The tracking device, in some cases, is configured to detect other types of signals from the medical device 106. For instance, the medical device 106 is configured to output a wireless signal that is detected by at least one transceiver of the tracking device. The wireless signal, for instance, may be an electromagnetic signal, an ultrasonic signal, or the like. In some cases, the tracking device detects the wireless signal from a tag 120 that is affixed to a housing of the medical device 106. For example, the tag 120 is a sticker or other type of label that is attached to the medical device 106. In some cases, the tag 120 includes a near-field communication (NFC) tag that emits an NFC signal detected by the tracking device.

In some cases, the tracking device includes an indication of the signal in the electronic record. For example, the tracking device includes an image of the medical device 106 in the electronic record, an audio file indicating the sound detected from the medical device 106, or an indication of the code 118 in the electronic record. In some cases, the indication of the signal provides context that enables a clinician later reviewing the electronic record to monitor and/or treat the patient 102 more effectively.

In various implementations, the medical device 106 determines an identifier of the medical device 106 based on the signal detected from the medical device 106 and/or the tag 120. In some examples, the medical device 106 analyzes the signal by comparing it to a prestored library of signals. In some cases, the medical device 106 stores a predictive model (e.g., an ML model) that the medical device 106 uses to identify the medical device 106. For instance, the tracking device may identify a manufacturer of the medical device 106, an identifier of the medical device 106, or a type of the medical device 106. Examples of the identifier include an identification (ID) code associated with the medical device

106, a manufacturer of the medical device 106, a model of the medical device 106, an owner of the medical device 106, a location of the medical device 106, or any combination thereof. In various implementations, the tracking device includes an identifier of the medical device 106 in the electronic record. In some cases, the identifier of the medical device 106 provides context that enables a clinician later reviewing the electronic record to monitor and/or treat the patient 102 more effectively.

In some examples, the tracking device detects an anomaly by inputting at least one image of the rescue scene 100 into an ML model, such as a CNN. For example, the ML model is trained using training data that includes multiple images of different types of anomalies as well as scenes that omit any relevant anomalies. In some cases, the ML model is a type of ML model suitable for anomaly detection, such as a Hidden Markov Model (HMM) Bayesian network, or replicator NN.

According to various implementations, the tracking device identifies a treatment administered by the medical device 106 to the patient 102. Examples of treatments include an electrical shock, pace pulse, chest compression, or assisted ventilation. For instance, the tracking device may recognize the treatment based on an image of the patient 102 at the time of the treatment, a sound emitted by the medical device 106 while treating the patient 102, an artifact in a physiological parameter detected by the tracking device from the patient 102, or via some other type of signal detected from the medical device 106 or the patient 102. In some cases, the tracking device determines a treatment parameter associated with the treatment. As used herein, the term "treatment parameter," and its equivalents, may refer to a metric that characterizes a treatment. Examples of treatment parameters include a voltage of an electrical shock administered to the patient 102, a frequency of chest compressions administered to the patient 102, a ventilation volume administered to the patient 102, or the like.

In some examples, the tracking device identifies information about the patient 102. The tracking device may recognize an identifier of the patient 102, such as a name, a medical condition, an age, a weight, a biological sex, a gender, a hair color, an eye color, or another type of identifier of the patient 102. In some cases, the tracking device detects a sound from the rescue scene 100 indicating a name or other identifying information about the patient 102. For example, the tracking device may detect a name spoken by the patient 102 or by another bystander in the vicinity of the patient 102. In some implementations, the rescuer 107 inputs the identifier of the patient 102 into the tracking device. According to various implementations, the tracking device detects the identifier by analyzing at least one image of the patient 102. For instance, the tracking device may input an image of the patient 102 into an ML model (e.g., a trained CNN) that is trained to recognize any of the above-noted identifiers of people depicted in images. The tracking device, in some examples, includes the identifier of the patient 102 in the electronic record.

In some implementations, the tracking device establishes a communication session with the medical device 106. For example, information encoded into the code 118, information visually presented in the image of the medical device 106, information encoded in the wireless signal received from the medical device 106, or information encoded into the signal received from the tag 120 enables the tracking device to establish the communication session with the medical device 106. In some cases, the communication session is a wireless communication session directly between the tracking device and the medical device 106. For example, the tracking device may perform pairing with the medical device 106. In some cases, the communication session is indirect. For example, the tracking device may communicate with the medical device 106 over an internet-mediated communication session, or over a cellular network-mediated communication session. In some examples, the tracking device communicates with the medical device 106 via one or more intermediary servers that are located remotely from the rescue scene 100.

According to various cases, the tracking device determines how to establish a communication session with the medical device 106 based on the identifier of the medical device 106. For example, the tracking device may identify an ID number of the medical device 106, such as by analyzing the image or receiving a signal indicating the ID number from the tag 120. The ID number, alone, may be insufficient information to establish a communication session. In some implementations, the tracking device stores or otherwise accesses a database that indicates how to connect to various medical devices based on their identifiers. For instance, the database may include multiple entries indexed by medical device identifier. By determining the identifier of the medical device 106, the tracking device may be able to identify an entry of the database that indicates connection information associated with the medical device 106. For example, the entry may include an address (e.g., an internet protocol (IP) address) of the medical device 106, an address of an intermediary device (e.g., a web server) that is configured to relay messages to the medical device 106, an encryption key for communications with the medical device 106, a wireless channel utilized by the medical device 106, or any other instructions that enable the tracking device to connect to the medical device 106.

The tracking device, in various cases, may receive information from the medical device 106 over the communication session. For example, the medical device 106 transmits an identifier of the medical device 106 to the tracking device over the communication session. In some cases, the medical device 106 transmits data indicative of the physiological parameter(s) that the medical device 106 detects from the patient 102. For example, the medical device 106 transmits a time at which the physiological parameter(s) were detected and/or values of the physiological parameter(s). In some implementations, the medical device 106 transmits a time at which a treatment was administered to the patient 102 and/or a treatment parameter associated with the treatment. The tracking device, for instance, includes indications of the physiological parameter(s) and/or treatment in the electronic record.

According to some cases, the tracking device detects other types of information about the rescue scene 100, the patient 102, or the medical device, and includes the other information in the electronic record. For example, the tracking device includes a location service circuit configured to detect a location of the tracking device, the patient 102, or the medical device 106. The location service circuit, for instance, includes a receiver configured to receive signals from satellites within a radionavigation system, such as the Global Positioning System (GPS), the Global Navigation Satellite System (GLONASS), BeiDou, or Galileo. These signals, in some cases, indicate the orbital positions of the broadcasting satellites as well as the times at which the signals were transmitted. The tracking device, for instance, can triangulate its location on the surface of the Earth based on the signals received from the satellites. In various cases, the tracking device includes an indication of the location in the electronic record.

In some implementations, the tracking device includes an identifier of the rescuer 107 in the electronic record. For instance, the rescuer 107 may enter the identifier into the tracking device, the tracking device may detect a badge (e.g., using NFC communication) associated with the rescuer 107, the tracking device may identify the rescuer 107 depicted in an image of the rescuer 107 (e.g., using at least one ML model), or the like. Examples of identifiers include the name of the rescuer 107 or another unique code (e.g., an alphanumeric code) associated with the rescuer 107 (e.g., an employee number).

In various cases, the tracking device generates or updates the electronic record to indicate an identifier of the medical device 106, an identifier of the patient 102, at least one physiological parameter of the patient 102, at least one treatment parameter characterizing a treatment administered by the medical device 106 to the patient 102, at least one time (e.g., 4 PM), at least one time interval (e.g., 20 minutes), a location of the tracking device or the medical device 106, an image of the patient 102, an image of the medical device 106, a sound detected in the rescue scene 100, an identifier of the rescuer 107, or any combination thereof. According to various implementations, the tracking device transmits the electronic record to an external device. The external device, in some implementations, includes one or more servers that are accessible from a clinical environment in which the patient 102 is later transferred. For example, the electronic record can be stored with an electronic medical record (EMR) associated with the patient 102.

Advantageously, implementations of the present disclosure enable the recording of clinically significant information in the rescue scene 100, even when the medical device 106 is inaccessible at a downstream clinical location. In some cases, the electronic record can provide important context about the medical device 106, even if the medical device is incapable of communicating data to external devices.

In some examples, a subsequent medical device 122 is utilized to monitor and/or treat the patient 102. For example, the medical device 106 is configured to be operated by an untrained user, such as an AED, and is used by a bystander to initially monitor and/or treat the patient 102. Subsequently, the rescuer 107 brings the subsequent medical device 122 into the rescue scene 100 to assist with care of the patient 102. The subsequent medical device 122, for instance, could be a monitor-defibrillator or another type of medical device that is utilized by a trained user.

In various implementations of the present disclosure, the subsequent medical device 122 includes one or more sensors configured to detect one or more physiological parameters of the patient 102. In addition, the subsequent medical device 122 includes a treatment component configured to administer a treatment to the patient 102.

According to some examples, the subsequent medical device 122 operates as a tracking device, as described herein. For example, the subsequent medical device 122 may generate an identifier of the medical device 106 and/or generate an identifier of the patient 102. Further, the subsequent medical device 122 may obtain patient-related data from the medical device 106, such as by establishing a communication channel with the medical device 106. In various cases, the subsequent medical device 122 can generate and/or modify an electronic record associated with the patient 102.

Further, the subsequent medical device 122 may include additional information in the electronic record. For example, the subsequent medical device 122, in some cases, includes, in the electronic record, an indication of the physiological parameter(s) detected by the subsequent medical device 122 and/or times at which the physiological parameter(s) are detected. In some examples, the subsequent medical device 122 administers a treatment to the patient 102 and indicates the treatment in the electronic record. For example, the subsequent medical device 122 includes a time at which the treatment was administered and/or one or more treatment parameters characterizing the treatment. Accordingly, in various implementations of the present disclosure, one medical device synthesizes patient data it generates with patient data generated by another medical device into a common electronic record that can be subsequently reviewed by a care provider at a downstream clinical environment.

Figure 2:
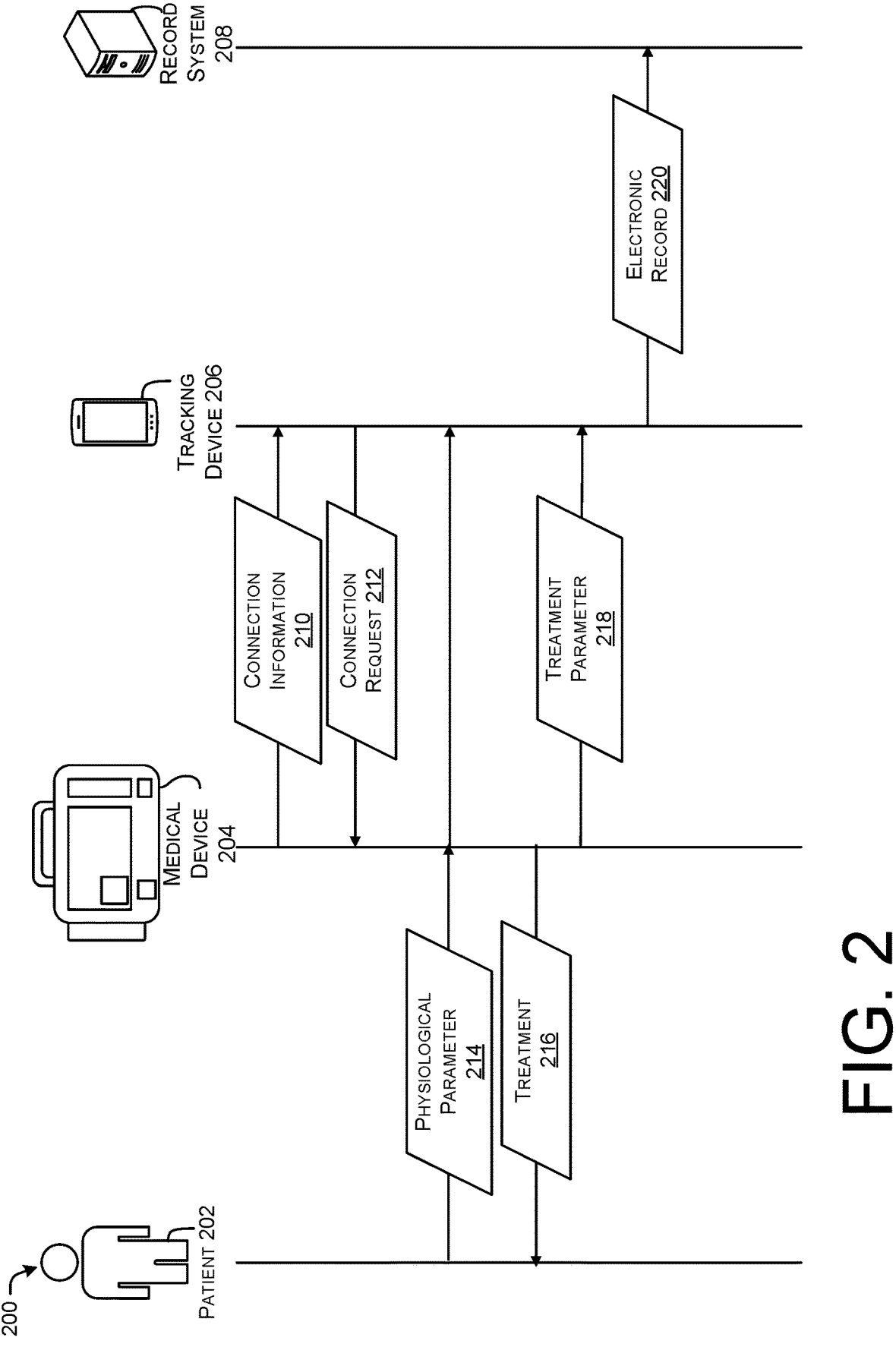
FIG. 2 illustrates example signaling for generating and transmitting a record of a rescue event.

FIG. 2 illustrates example signaling 200 for generating and transmitting a record of a rescue event. As shown, the signaling 200 is between a patient 202 (e.g., the patient 102), a medical device 204 (e.g., the medical device 106, optionally in combination with the tag 120), a tracking device 206 (e.g., the mobile device 110, the wearable device 112, the robot 114, the UAV 116, the subsequent medical device 112, or any combination thereof), and a record system 208. In various implementations, the record system 208 includes one or more computing devices that are located remotely from the patient 102, the medical device 204, and the tracking device 206. For example, the record system may be embodied by one or more web servers that are communicatively coupled to the Internet.

The tracking device 206 receives connection information 210 from the medical device 204. In various implementations, the connection information 210 enables the tracking device 206 to establish a communication session with the medical device 204. As used herein, the terms "session," "communication session," and their equivalents, may refer to a unidirectional or bidirectional flow of data between multiple endpoints. Using the connection information 210, the tracking device 206 is configured to transmit and/or receive communication signals with the medical device 204 over a communication channel. As used herein, the terms "channel," "communication channel," and their equivalents, may refer to a physical or logical transmission medium over which data can be transmitted between multiple endpoints. Signals that are transmitted over the communication channel and that encode data may be referred to as "communication signals."

In some cases, the connection information 210 includes an identifier of the medical device 204. For example, the connection information 210 includes an internet protocol (IP) address and/or a media access control (MAC) address of the medical device 204. In some implementations, the connection information 210 indicates a communication capability of the medical device 204. For instance, the connection information 210 indicates that the medical device 204 includes a transceiver configured to transmit and/or receive communication signals over BLUETOOTH, NFC, WI-FI, a 3GPP network, or ultrasound-based communication. In some examples, the connection information 210 identifies a communication channel over which the medical device 204 is configured to communicate. For example, the connection information 210 indicates that the medical device 204 is configured to transmit and/or receive communication signals within a particular electromagnetic frequency range.

According to particular examples, the connection information 210 includes pairing information. As used herein, the term "pairing information," and its equivalents, can refer to data that enables multiple devices to be paired. As used herein, the term "paired," and its equivalents, may refer to a state of multiple devices that have a shared link key that enables each device to cryptographically authenticate data it receives from any other device among the multiple devices.

In particular cases, a first paired device encrypts data prior to transmitting the data to a second paired device, and the second paired device restores the original data by decrypting the encrypted data. As used herein, the term "encrypt," and its equivalents, refers to a process of translating data from one format (e.g., an unencoded format) into an encoded format. In various cases, the encoded format is referred to as "ciphertext." Unencoded data, which has not been encrypted, may be referred to as being in "plaintext." In various examples, an entity encrypts data using at least one encryption key. An encryption key is a parameter that defines the translation of data from the one format into the encoded format. As used herein, the term "decrypt," and its equivalents, refers to a process of translating data from an encoded format into another format (e.g., an unencoded format), such as a plaintext format. In various examples, an entity encrypts data using at least one decryption key. A decryption key is a parameter that defines the translation of data from the encoded format into the other format. A link key, for example, is an encryption and/or decryption key.

Various cryptographic techniques can be utilized in accordance with the features described in this disclosure. For example, data can be encrypted and decrypted via a symmetric key, wherein the encryption key and the decryption key are equivalent. In some cases, data can be encrypted and decrypted via asymmetric keys, wherein the encryption key and the decryption key are different. Cryptographic hash functions (CHFs) are examples of cryptographic techniques. Examples of cryptographic techniques include the Data Encryption Standard (DES), Advanced Encryption Standard (AES), Elliptic Curve Cryptography (ECC), Rivest-Shamir-Adleman (RSA), Secure Hash Algorithm (SHA)-1, SHA-2, SHA-3, BLAKE, BLAKE2, BLAKE3, WHIRLPOOL, MD2, MD4, MD5, MD6, Temporal Key Integrity Protocol (TKIP), Rivest cipher 4 (RC4), variably modified permutation composition (VMPC), blowfish, Twofish, Threefish, Tiny Encryption Algorithm (TEA), Extended TEA (XTEA), Corrected Block TEA (XXTEA), Diffie-Hellman exchange (DHE), elliptic curve DHE, supersingular isogeny Diffie-Hellman (SIDH) key exchange, and so on. Any suitable encryption or decryption technique can be used in accordance with implementations of this disclosure.

In some implementations, the connection information 210 includes or otherwise indicates an encryption key suitable for subsequent communication signals transmitted between the medical device 204 and the tracking device 206. The connection information 210, according to some cases, is part of a handshake between the medical device 204 and the tracking device 206. As used herein, the term "handshake," and its equivalents, refers to one or more signals transmitted between at least two endpoints that establish protocols of communication between the endpoints (e.g., prior to substantive data being exchanged between the endpoints). The medical device 204 and the tracking device 206, in some cases, utilize Transmission Control Protocol (TCP). TCP, for instance, utilizes handshakes to establish communication sessions between devices. For example, a first device transmits a synchronize message including a first sequence number to a second device. The second device, in turn, transmits a synchronize-acknowledgement message including a second sequence number as well as a first acknowledgement number that is one greater than the first sequence number. In response, the first device transmits an acknowledgement message including a second acknowledgment number that is one greater than the second sequence number to the second device. The first and second devices, in some examples, are paired once the first device transmits the acknowledgement message. The sequence and acknowledgement numbers are used to initialize counters that track messages and/or bytes of data transmitted between the paired devices.

In some examples, the connection information 210 includes or otherwise indicates a link key that enables the tracking device 206 to pair with the medical device 204. The medical device 204, for instance, broadcasts the connection information 210. In some examples, the medical device 204 broadcasts the connection information 210 in response to receiving an input signal from a user, in response to being powered on, in response to initiating the treatment, or the like.

In some implementations, the connection information 210 is output by the medical device 204. For instance, the medical device 204 includes a transceiver that transmits a communication signal encoding the connection information 210 to the tracking device 206. In some implementations, the connection information 210 is transmitted by a tag affixed to a housing of the medical device 204. For example, the tag may be a sticker or other passive element that is physically coupled to at least one additional component of the medical device 204. In various implementations, the tag includes an NFC chip that transmits the connection information 210 when powered by an external electromagnetic (EM) field, such as an EM field generated by the tracking device 206.

According to some implementations, the connection information 210 is displayed by the medical device 204. For example, the tracking device 206 detects the connection information 210 by capturing an image of the medical device 204. In some implementations, the connection information 210 is encoded in a barcode (e.g., a QR code) that is printed on a housing of the medical device 204, printed on a tag affixed to the medical device 204, or visually output on a display of the medical device 204. In some cases, the connection information 210 is encoded in a sound output by a speaker of the medical device 204 and detected by a microphone of the tracking device 206.

Based on the connection information 210, the tracking device 206 transmits a connection request 212 to the medical device 204. In various implementations, the connection request 212 is a request to establish the communication channel between the medical device 204 and the tracking device 206. In some cases, the connection request 212 includes a pairing request that enables the tracking device 206 to pair with the medical device 204. For example, the connection request 212 may include a message encrypted according to at least one encryption key indicated in the connection information 210 or may include a synchronize acknowledgement message.

In some implementations, the connection request 212 includes a request for data stored by the medical device 204. For example, the connection request 212 may cause the medical device 204 to transmit a communication signal encoding data associated with a patient and/or data associated with the medical device 204.

In various implementations, the medical device 204 detects a physiological parameter 214 from the patient 202. In response to receiving the connection request 212, the medical device 204 may forward the physiological parameter to the tracking device 206. In various implementations, the physiological parameter 214 is represented by data that indicates a physiological parameter detected at a particular sampling frequency, detected repeatedly, or detected at a single time.

Further, in various cases, the medical device 204 administers a treatment 216 to the patient 202. For example, the medical device 204 administers at least one of an electrical shock (e.g., a defibrillation treatment), pace pulses, chest compressions, assisted ventilation, or a medication. In some cases, the medical device 204 administers the treatment 216 based on an analysis of the physiological parameter 214. For example, the medical device 204 administers an electrical shock to the patient 202 in response to detecting a shockable arrhythmia indicated by an ECG of the patient 202.

The medical device 204, in various implementations, transmits a treatment parameter 218 to the tracking device 206. The treatment parameter 218, for instance, characterizes the treatment 216 administered to the patient 202. In some implementations, the treatment parameter 218 indicates a time and/or frequency at which the treatment 216 is administered. In some cases, the treatment parameter 218 indicates a magnitude of the treatment 216. For example, the treatment parameter 218 indicates a voltage of an electrical shock or pace pulses administered to the patient 202, a medication dosage, a ventilation pressure, a ventilation flow rate, a chest compression pressure, or the like.

In various implementations, the tracking device 206 generates and/or transmits an electronic record 220. The electronic record 220, for instance, is transmitted to the record system 208. In some implementations, the electronic record 220 indicates the physiological parameter 214 and/or the treatment parameter 218. In some cases, the electronic record 220 indicates additional detail about the patient 202 and/or the medical device 204, such as demographic information about the patient 202, a location of the patient 202, a manufacturer of the medical device 204, a model of the medical device 204, a type of the medical device 204, or any combination thereof. In some cases, the tracking device 206 detects and/or receives additional parameters associated with the patient 202, and includes the additional parameters in the electronic record 220.

In some implementations, the record system 208 stores the electronic record 220 for future reference, such as by a clinician treating the patient 202 at a later time. In some cases, the record system 208 transmits at least a portion of the electronic record 220 to another device, such as a computing device operated by one or more clinicians treating the patient 202. Accordingly, the electronic record 220 enhances continuity of the care of the patient 202.

Figure 3:
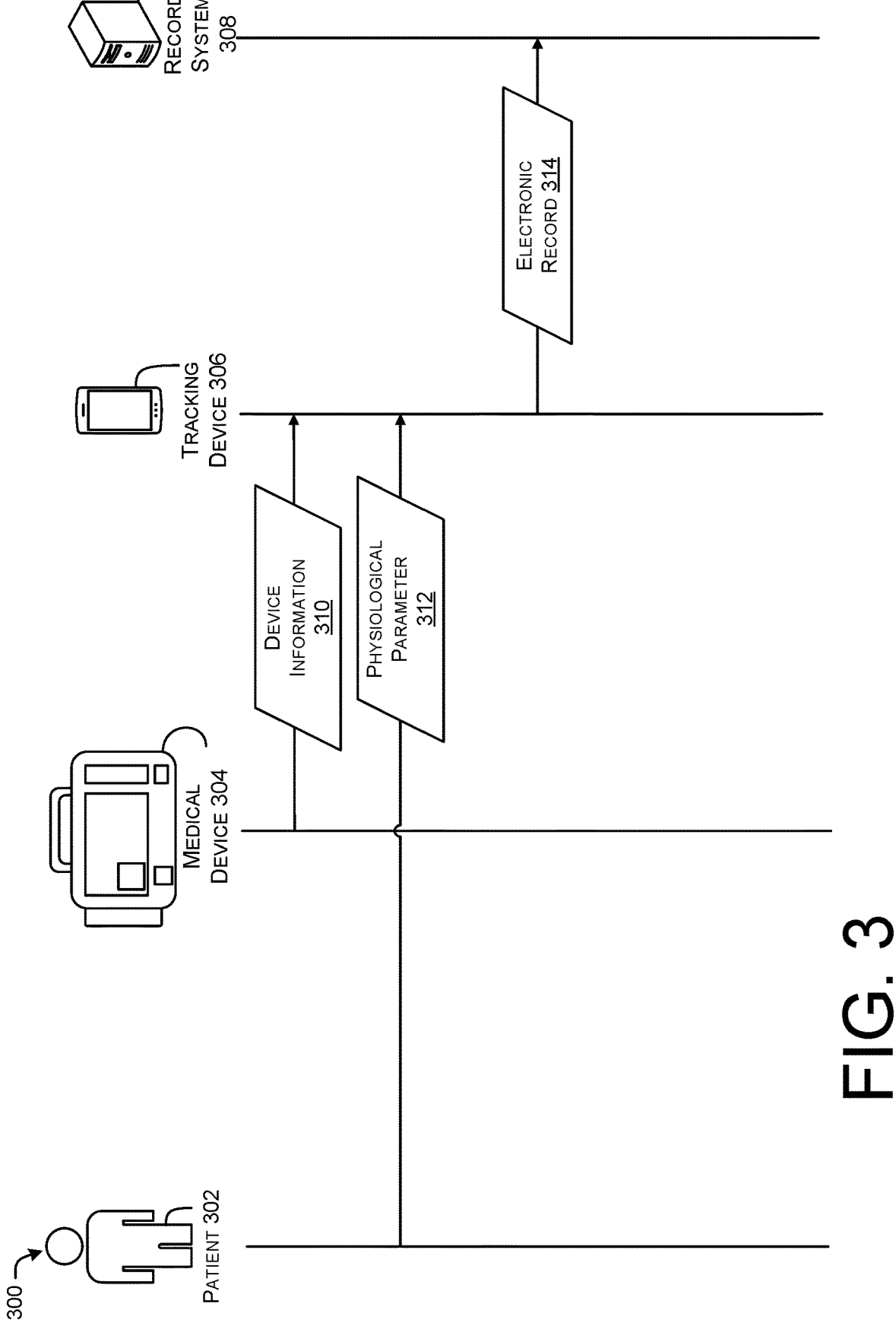
FIG. 3 illustrates example signaling for generating and transmitting a record of a rescue event.

FIG. 3 illustrates example signaling 300 for generating and transmitting a record of a rescue event. As shown, the signaling 300 is between a patient 302 (e.g., the patient 102), a medical device 304 (e.g., the medical device 106, optionally in combination with the tag 120), a tracking device 306 (e.g., the mobile device 110, the wearable device 112, the robot 114, the UAV 116, the subsequent medical device 112, or any combination thereof), and a record system 308. In various implementations, the record system 308 includes one or more computing devices that are located remotely from the patient 302, the medical device 304, and the tracking device 306. For example, the record system may be embodied by one or more web servers that are communicatively coupled to the Internet. In some examples, the medical device 304 is not configured to communicate with the tracking device 306 directly, such as through a wireless communication channel.

In various implementations, the tracking device 306 receives device information 310 from the medical device 304. The device information 310, for example, indicates information associated with the medical device 304. In some implementations, the device information 310 indicates a manufacturer of the medical device 304, a model of the medical device 304, a type of the medical device 304 (e.g., whether the medical device 304 is an AED or a mechanical chest compression device), or any combination thereof. According to some implementations, the device information 310 includes communication information that enables the tracking device 306 to exchange data with the medical device 304.

In some cases, the device information 310 indicates an identifier associated with the medical device 304. For instance, the medical device 304 is uniquely associated with an alphanumeric ID code that is indicated in the device information 310. In some implementations, the medical device 304 is part of a fleet of medical devices, such as a fleet owned and/or operated by the same entity. In various cases, each medical device in the fleet, including the medical device 304, is associated with a unique identifier.

In some implementations, the medical device 304 transmits a signal to the tracking device 306 indicating the device information 310. For instance, the medical device 304 transmits the device information 310 in a communication signal over a communication channel with the tracking device 306.

In particular cases, the tracking device 306 detects the device information 310 by an alternate means. For example, the tracking device 306 may capture an image of the medical device 304 via a camera, and may identify the device information 310 based on the image. In some implementations, the tracking device 306 identifies the device information 310 by analyzing the image. In some cases, the image depicts a code (e.g., a QR code) encoding the device information 310. According to some examples, the tracking device 306 identifies the device information 310 by performing image recognition on the image. For example, the tracking device 306 identifies a manufacturer, model, or type of the medical device 304 by comparing the image to one or more images of other medical devices and/or by inputting the image into an ML model.

According to various examples, the tracking device 306 detects the device information 310 by detecting a sound by the medical device 304. For instance, the medical device 304 may compare an audible prompt, alarm sound, on sound, off sound, or other sound detected from the medical device 304 to a predetermined set of sounds from other medical devices in order to identify the medical device 304. In some cases, the tracking device 306 identifies the device information 310 by inputting the sound into a trained ML model.

In some implementations, the tracking device 306 further detects a physiological parameter 312 from the patient 302. For instance, the tracking device 306 may include and/or be communicatively coupled to a sensor configured to detect the physiological parameter 312. In some cases, the tracking device 306 detects a sound indicating a state of the patient 302 and/or the tracking device 306 captures an image of the patient 302 that indicates a state of the patient 302.

According to various implementations, the tracking device 306 generates an electronic record 314 based on the device information 310 and/or the physiological parameter 312. In some examples, the electronic record 314 includes text data indicating the device information 310, the physiological parameter 312, a time (e.g., at which the tracking device 306 receives the device information 310 and/or physiological parameter 312), a location of the tracking device 306, or any combination thereof. In some implementations, the electronic record 314 includes at least a portion of the image and/or sound detected by the tracking device 306. In some cases, a rescuer enters additional notes about the patient 302 and/or the medical device 304 into the tracking device 306 (e.g., via a keypad or touch screen), and the electronic record 314 further indicates the additional notes. The tracking device 30 transmits the electronic record 314 to the record system 308.

In some implementations, the record system 308 stores the electronic record 314 for future reference, such as by a clinician treating the patient 302 at a later time. In some cases, the record system 308 transmits at least a portion of the electronic record 314 to another device, such as a computing device operated by one or more clinicians treating the patient 302. Accordingly, the electronic record 314 enhances continuity of the care of the patient 302.

Figure 4:
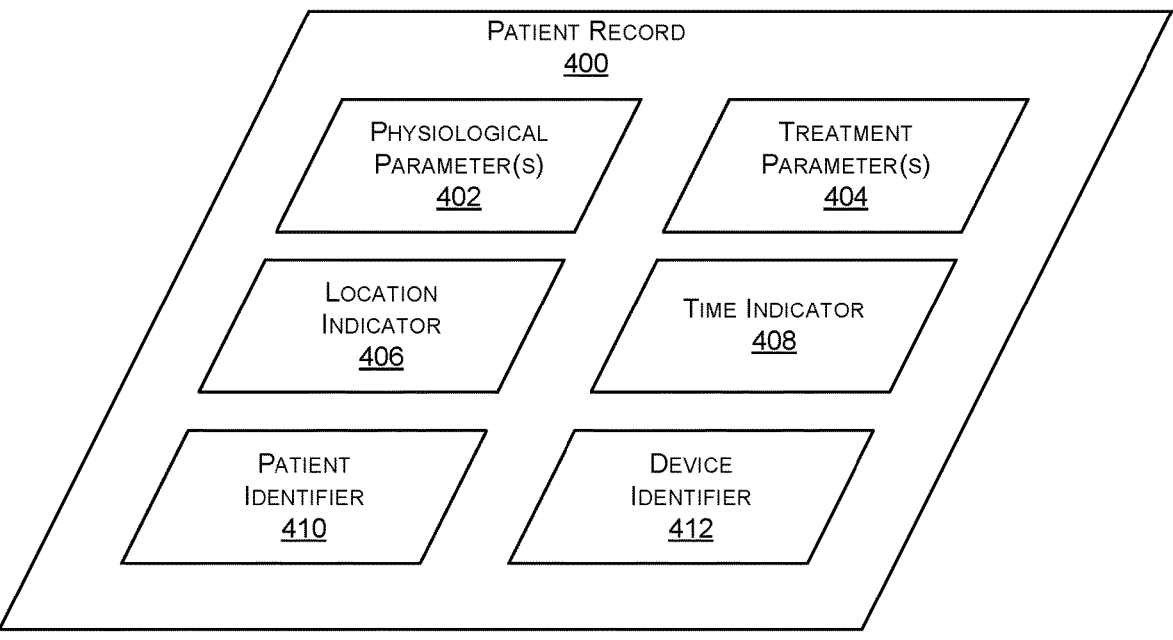
FIG. 4 illustrates an example of a patient record.

FIG. 4 illustrates an example of a patient record 400. In various implementations, the patient record includes at least one physiological parameter 402, at least one treatment parameter 404, a location indicator 406, a time indicator 408, a patient identifier 410, a device identifier 412, or any combination thereof. In various cases, the patient record 400 includes text data. In some cases, the patient record 400 includes at least one digital image and/or a sound file.

The physiological parameter(s) 402, in various cases, are detected from a patient that was monitored and/or treated by a medical device. In various examples, the physiological parameter(s) 402 include at least one physiological parameter detected by the medical device and/or by a tracking device. In some cases, the tracking device is another medical device that is used to subsequently monitor and/or treat the patient.

The treatment parameter(s) 404 indicate at least one treatment administered to the patient. For instance, the treatment is administered by the medical device, by another medical device, or directly by a rescuer.

The location indicator 406 represents a position corresponding to the patient, the medical device, or the tracking device. For example, the location indicator 406 indicates an access point (AP) communicatively coupled to the medical device and/or the tracking device. In some cases, the location indicator 406 is generated using a location service circuit, such as by a device including a GPS receiver.

The time indicator 408 represents a time of a patient event. For example, the time indicator 408 includes a time at which the medical device was initially attached to the patient, a time at which the physiological parameter(s) 402 were detected, a time at which the treatment was administered, a time at which the patient was disconnected from the medical device, a time interval since an event (e.g., a treatment was performed or a parameter detected), or the like.

In various implementations, the patient identifier 410 indicates an identity of the patient. In some cases, the patient identifier 410 includes a name of the patient, demographic information about the patient, or an identifier associated with an event in which a rescuer responds to a medical emergency associated with the patient. For example, the patient identifier 410 may indicate that the patient was associated with a particular emergency call received at a particular time, even if the name of the patient is unknown.

The device identifier 412 indicates the medical device and/or the tracking device. In various implementations, the device identifier 412 indicates a unique ID code associated with the medical device.

Figure 5:
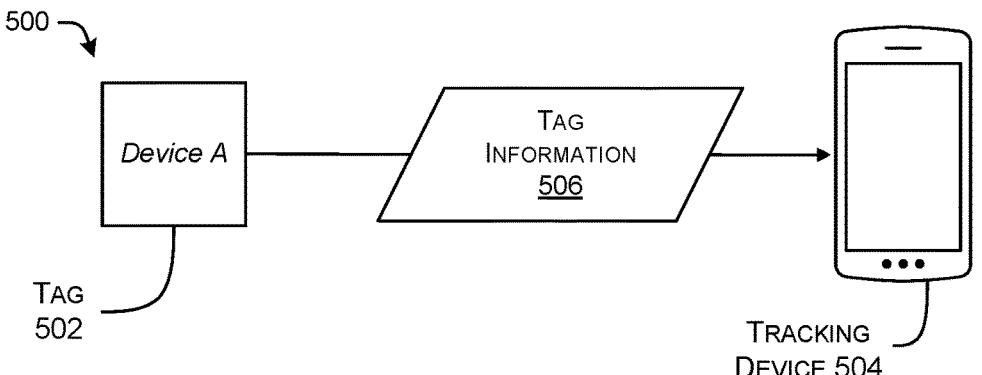
FIG. 5 illustrates example signaling between a tag and a tracking device.

FIG. 5 illustrates example signaling 500 between a tag 502 and a tracking device 504. In various cases, the tag 502 is physically associated with a medical device. For instance, the tag 502 is glued to a housing of the medical device, the tag 502 is a sticker that is attached to the housing of the medical device, the tag 502 is tied or otherwise strapped to the medical device, or the like. According to some cases, the tag 502 is physically printed with an identifier of the medical device. For instance, as illustrated in FIG. 5, the tag 502 is printed with the words "Device A," which is an identifier of the medical device.

In some examples, the tag 502 includes a passive transmitter. For example, the tag 502 includes an NFC chip that is powered when in the presence of an activating electrical field. The electrical field, for instance, is output by the tracking device 504.

In various implementations, the tag 502 is configured to transmit tag information 506 to the tracking device 504. In various cases, the tag information 506 is transmitted over a wireless communication channel. According to some examples, the tag information 506 indicates the tag 502 and/or the medical device associated with the tag 502. For example, the tag information 506 includes a code (e.g., an alphanumeric code) that is uniquely associated with the tag 502 among a group of tags and/or is uniquely associated with the medical device among a fleet of medical devices. For instance, the tag information 506 may indicate that the tag 502 is affixed to Device A.

According to some cases, the tag 502 may be affixed or otherwise physically associated with a medical device that is not configured to communicate with the tracking device 504. Thus, the tag 502 may communicate at least one feature of the medical device in the tag information 506. In some cases, the tracking device 504 is configured to generate an electronic record based on the tag information 506.

In a particular example, the tag 502 is affixed to an AED that does not have WI-FI or other wireless communication capabilities. The tracking device 504 may be associated with a rescuer that arrives to a rescue scene after the AED has been used to monitor and/or treat the patient. In various cases, the tracking device 504 detects the tag information 506 from the tag 502 and generates an electronic record based on the tag information 506. For instance, by including a unique identifier of the tag 502 and/or the medical device, a later care provider may be provided clinically relevant context of the condition of the patient.

Figure 6A:
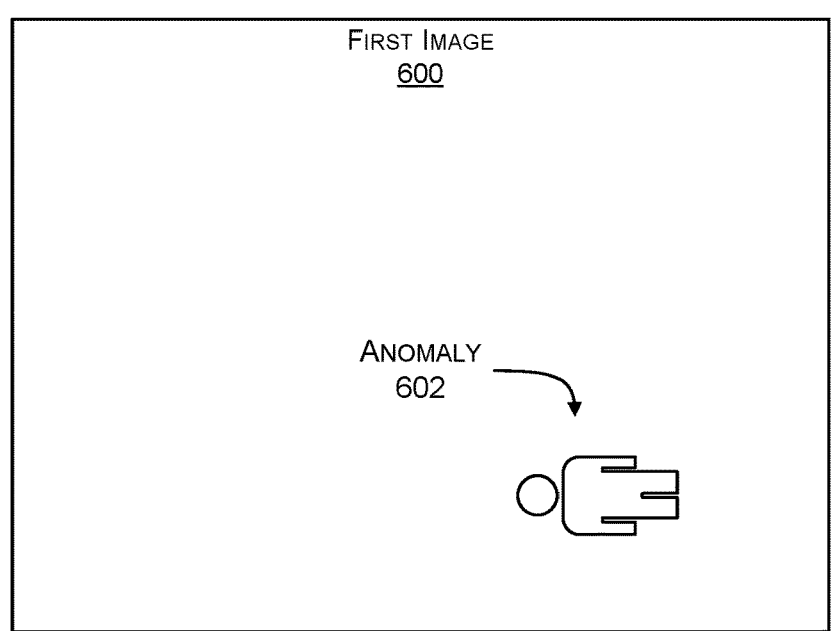
FIGS. 6A and 6B illustrate example images detected by a tracking device configured to move itself throughout a rescue scene.
Figure 6B:
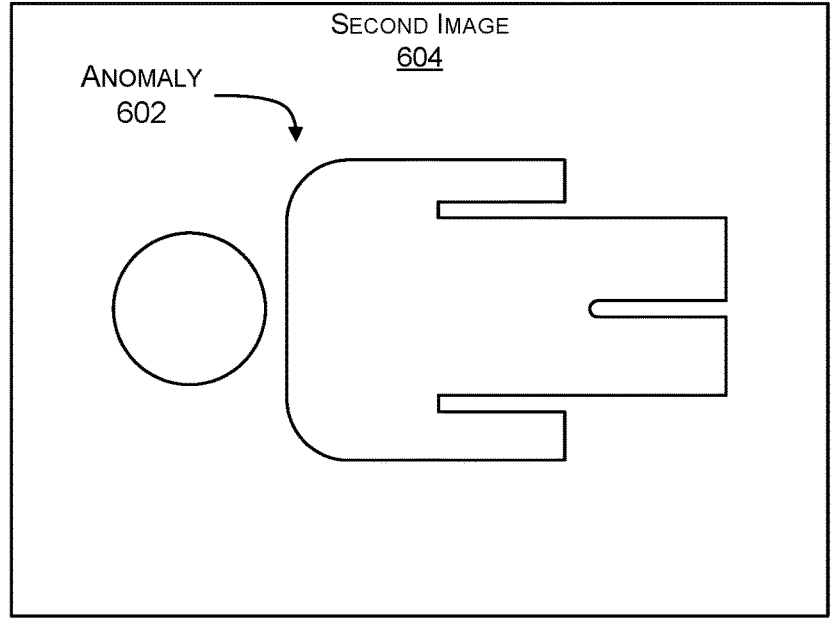

FIGS. 6A and 6B illustrate example images detected by a tracking device configured to move itself throughout a rescue scene. For example, the images are captured by a robot or UAV surveilling a rescue scene.

FIG. 6A illustrates a first image 600 captured by the tracking device at a first time. The first image 600 depicts an anomaly 602. Various types of anomalies are possible, such as a person being in a collapsed position, a person being injured, a dangerous condition (e.g., a downed powerline, debris, an explosion, or the like), or any combination thereof. In various cases, the anomaly 602 is indicative that a person is in need of emergency medical care.

According to various implementations, the tracking device identifies the anomaly 602 by analyzing the first image 600. In various cases, the tracking device performs anomaly detection. In various cases, the tracking device identifies the anomaly 602 by inputting the first image 600 into one or more trained ML models.

Once the tracking device detects the anomaly 602, in some cases, the tracking device moves itself to a location proximate to the anomaly 602. In various cases, the tracking device moves closer to the anomaly 602. In some cases, the tracking device includes a movement component (e.g., a propeller, a robotic leg, a wheel, etc.) that the tracking device controls to move closer to the anomaly 602.

FIG. 6B illustrates a second image 604 captured by the tracking device at a second time. As illustrated, the second image 604 depicts the anomaly 602 from a closer vantage point than the first image 600.

FIG. 7 illustrates an example process 700 for generating an electronic record. The process 700 may be performed by an entity including a tracking device, another medical device, a mobile device, a wearable device, a robot, a UAV, at least one processor, or any combination thereof.

At 702, the entity identifies a medical device and/or patient associated with the medical device. In various implementations, the entity detects a signal and identifies the medical device and/or the patient based on the signal. For example, the entity captures an image depicting the medical device, detects a sound output by the medical device, or receives a communication signal from the medical device. In various implementations, the signal itself indicates the medical device and/or the patient. In some implementations, the entity infers an identifier of the medical device or an identifier of the patient based on the signal. In various implementations, the identifier of the medical device includes an ID number of the medical device, a manufacturer of the medical device, a model of the medical device, or even a portion of the signal detected by the entity that indicates the medical device. According to some examples, the identifier of the patient includes demographic information about the patient, a condition of the patient, a name of the patient, or the like.

At 704, the entity generates an electronic record indicating the medical device and/or the patient. In various implementations, the electronic record includes an identifier of the medical device, an identifier of the patient, or a combination thereof. In various implementations, the electronic record indicates the signal detected by the entity, such as the image or a file indicating the sound.

At 706, the entity outputs the electronic record. In some implementations, the entity displays the electronic record. In some cases, the entity transmits the electronic record to an external device. For example, the entity includes a transceiver that transmits a signal encoding the electronic record over one or more communication networks.

FIG. 8 illustrates an example process 800 for generating an electronic record based on communication with a medical device. The process 800 may be performed by an entity including a tracking device, another medical device, a mobile device, a wearable device, a robot, a UAV, at least one processor, or any combination thereof.

At 802, the entity identifies connection information associated with the medical device. In some cases, the entity detects a signal from the medical device indicating the connection information. In various implementations, the entity identifies the connection information by receiving a communication signal indicating the connection information from a tag affixed to a housing of the medical device. In some implementations, the entity captures an image of the medical device and identifies the connection information by analyzing the image. For instance, the entity detects an ID number, a QR code, or some other visual characteristic of the medical device that is depicted in the image.

The connection information, in various implementations, includes information that enables the entity to communicate with the medical device. In some cases, the connection information includes an address of the medical device, a communication channel utilized by the medical device, a communication protocol utilized by the medical device. In some implementations, the connection information specifies an encryption key. In various cases, the medical device is configured to decrypt data that is encrypted using the encryption key indicated by the connection information.

At 804, the entity establishes a communication session with the medical device based on the connection information. For example, the entity transmits a message that is addressed to the address of the medical device. In some cases, the entity transmits a message using the communication channel and communication protocol utilized by the medical device. In various implementations, the entity transmits a message that includes data encrypted using the encryption key. According to some cases, the entity transmits, over the communication session, a request for information about the medical device or a patient associated with the medical device. In various implementations, the communication session includes communications between the medical device and the entity that are distinct from the signal indicating the communication information. For instance, the entity detects the communication information by analyzing an image of the medical device or by receiving an NFC signal from the medical device, whereas the communication session is over a BLUETOOTH, WI-FI, or cellular network communication channel.

At 806, the entity receives, from the medical device over the communication channel, record information about the medical device and/or the patient associated with the medical device. In some cases, the record information includes an identifier of the medical device. For example, the identifier of the medical device includes an ID code associated with the medical device, a type of the medical device, a manufacturer of the medical device, a serial number of the medical device, a model of the medical device, or the like. In various implementations, the record information includes an identifier of the patient. For example, an identifier of the patient is a name of the patient, a demographic of the patient, or some other characteristic of the patient. In various implementations, the record information includes at least one physiological parameter of the patient that was detected by the medical device. In some examples, the record information includes at least one treatment parameter characterizing a treatment that was administered to the patient by the medical device.

At 808, the entity generates an electronic record based on the record information. In various implementations, the electronic record includes data that indicates at least a portion of the record information. In some cases, the electronic record includes additional information, such as a location of the entity, a time, an identifier of a user of the entity, or another physiological parameter of the patient that was detected by the entity.

Figure 9:
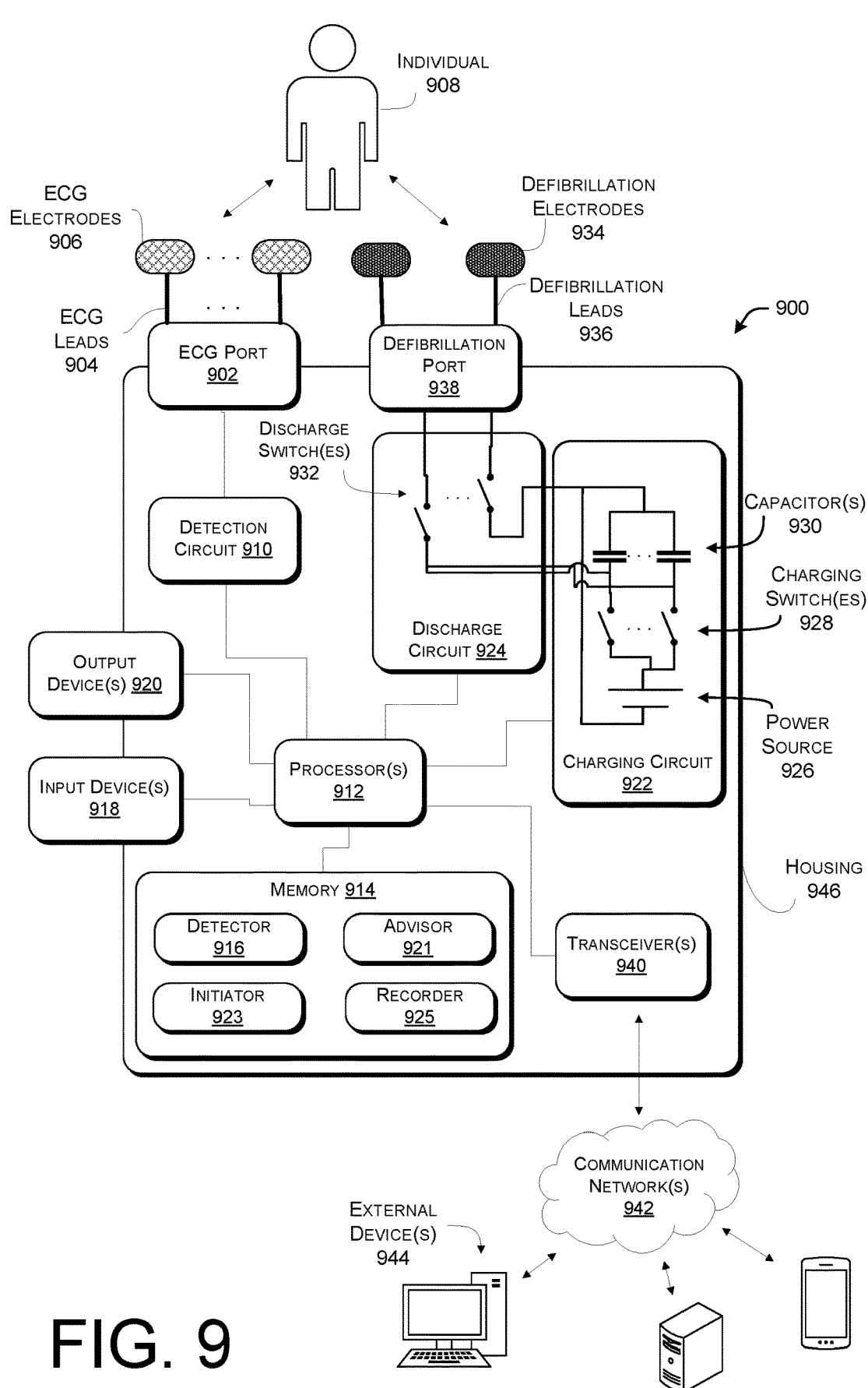
FIG. 9 illustrates an example of an external defibrillator configured to perform various functions described herein.

FIG. 9 illustrates an example of an external defibrillator 900 configured to perform various functions described herein. For example, the external defibrillator 900 is the medical device 106 or subsequent medical device 122 described above with reference to FIG. 1.

The external defibrillator 900 includes an electrocardiogram (ECG) port 902 connected to multiple ECG leads 904.

In some cases, the ECG leads 904 are removeable from the ECG port 902. For instance, the ECG leads 904 are plugged into the ECG port 902. The ECG leads 904 are connected to ECG electrodes 906, respectively. In various implementations, the ECG electrodes 906 are disposed on different locations on an individual 908. A detection circuit 910 is configured to detect relative voltages between the ECG electrodes 906. These voltages are indicative of the electrical activity of the heart of the individual 908.

In various implementations, the ECG electrodes 906 are in contact with the different locations on the skin of the individual 908. In some examples, a first one of the ECG electrodes 906 is placed on the skin between the heart and right arm of the individual 908, a second one of the ECG electrodes 906 is placed on the skin between the heart and left arm of the individual 908, and a third one of the ECG electrodes 906 is placed on the skin between the heart and a leg (either the left leg or the right leg) of the individual 908. In these examples, the detection circuit 910 is configured to measure the relative voltages between the first, second, and third ECG electrodes 906. Respective pairings of the ECG electrodes 906 are referred to as "leads," and the voltages between the pairs of ECG electrodes 906 are known as "lead voltages." In some examples, more than three ECG electrodes 906 are included, such that 5-lead or 12-lead ECG signals are detected by the detection circuit 910.

The detection circuit 910 includes at least one analog circuit, at least one digital circuit, or a combination thereof. The detection circuit 910 receives the analog electrical signals from the ECG electrodes 906, via the ECG port 902 and the ECG leads 904. In some cases, the detection circuit 910 includes one or more analog filters configured to filter noise and/or artifact from the electrical signals. The detection circuit 910 includes an analog-to-digital (ADC) in various examples. The detection circuit 910 generates a digital signal indicative of the analog electrical signals from the ECG electrodes 906. This digital signal can be referred to as an "ECG signal" or an "ECG."

In some cases, the detection circuit 910 further detects an electrical impedance between at least one pair of the ECG electrodes 906. For example, the detection circuit 910 includes, or otherwise controls, a power source that applies a known voltage (or current) across a pair of the ECG electrodes 906 and detects a resultant current (or voltage) between the pair of the ECG electrodes 906. The impedance is generated based on the applied signal (voltage or current) and the resultant signal (current or voltage). In various cases, the impedance corresponds to respiration of the individual 908, chest compressions performed on the individual 908, and other physiological states of the individual 908. In various examples, the detection circuit 910 includes one or more analog filters configured to filter noise and/or artifact from the resultant signal. The detection circuit 910 generates a digital signal indicative of the impedance using an ADC. This digital signal can be referred to as an "impedance signal" or an "impedance."

The detection circuit 910 provides the ECG signal and/or the impedance signal to one or more processors 912 in the external defibrillator 900. In some implementations, the processor(s) 912 includes a central processing unit (CPU), a graphics processing unit (GPU), both CPU and GPU, or other processing unit or component known in the art.

The processor(s) 912 is operably connected to memory 914. In various implementations, the memory 914 is volatile (such as random access memory (RAM)), non-volatile (such as read only memory (ROM), flash memory, etc.) or some combination of the two. The memory 914 stores instructions that, when executed by the processor(s) 912, causes the processor(s) 912 to perform various operations. In various examples, the memory 914 stores methods, threads, processes, applications, objects, modules, any other sort of executable instruction, or a combination thereof. In some cases, the memory 914 stores files, databases, or a combination thereof. In some examples, the memory 914 includes RAM, ROM, electrically erasable programmable read-only memory (EEPROM), flash memory, or any other memory technology. In some examples, the memory 914 includes one or more of CD-ROMs, digital versatile discs (DVDs), content-addressable memory (CAM), or other optical storage, magnetic cassettes, magnetic tape, magnetic disk storage or other magnetic storage devices, or any other medium which can be used to store the desired information and which can be accessed by the processor(s) 912 and/or the external defibrillator 900. In some cases, the memory 914 at least temporarily stores the ECG signal and/or the impedance signal.

In various examples, the memory 914 includes a detector 916, which causes the processor(s) 912 to determine, based on the ECG signal and/or the impedance signal, whether the individual 908 is exhibiting a particular heart rhythm. For instance, the processor(s) 912 determines whether the individual 908 is experiencing a shockable rhythm that is treatable by defibrillation. Examples of shockable rhythms include ventricular fibrillation (VF) and ventricular tachycardia (V-Tach). In some examples, the processor(s) 912 determines whether any of a variety of different rhythms (e.g., asystole, sinus rhythm, atrial fibrillation (AF), etc.) are present in the ECG signal.

The processor(s) 912 is operably connected to one or more input devices 918 and one or more output devices 920. Collectively, the input device(s) 918 and the output device(s) 920 function as an interface between a user and the defibrillator 900. The input device(s) 918 is configured to receive an input from a user and includes at least one of a keypad, a cursor control, a touch-sensitive display, a voice input device (e.g., a microphone), a haptic feedback device (e.g., a gyroscope), or any combination thereof. The output device(s) 920 includes at least one of a display, a speaker, a haptic output device, a printer, or any combination thereof. In various examples, the processor(s) 912 causes a display among the input device(s) 918 to visually output a waveform of the ECG signal and/or the impedance signal. In some implementations, the input device(s) 918 includes one or more touch sensors, the output device(s) 920 includes a display screen, and the touch sensor(s) is integrated with the display screen. Thus, in some cases, the external defibrillator 900 includes a touchscreen configured to receive user input signal(s) and visually output physiological parameters, such as the ECG signal and/or the impedance signal. In some cases, the input device(s) 918 include a camera or microphone configured to capture an image or sound of the subject individual 906 or another medical device. The input device(s) 918, in some cases, include additional sensors configured to detect other types of physiological parameters of the individual 906.

In some examples, the memory 914 includes an advisor 921, which, when executed by the processor(s) 912, causes the processor(s) 912 to generate advice and/or control the output device(s) 920 to output the advice to a user (e.g., a rescuer). In some examples, the processor(s) 912 provides, or causes the output device(s) 920 to provide, an instruction to perform CPR on the individual 908. In some cases, the processor(s) 912 evaluates, based on the ECG signal, the impedance signal, or other physiological parameters, CPR being performed on the individual 908 and causes the output device(s) 920 to provide feedback about the CPR in the instruction. According to some examples, the processor(s) 912, upon identifying that a shockable rhythm is present in the ECG signal, causes the output device(s) 920 to output an instruction and/or recommendation to administer a defibrillation shock to the individual 908.

The memory 914 also includes an initiator 923 which, when executed by the processor(s) 912, causes the processor(s) 912 to control other elements of the external defibrillator 900 in order to administer a defibrillation shock to the individual 908. In some examples, the processor(s) 912 executing the initiator 923 selectively causes the administration of the defibrillation shock based on determining that the individual 908 is exhibiting the shockable rhythm and/or based on an input from a user (received, e.g., by the input device(s) 918). In some cases, the processor(s) 912 causes the defibrillation shock to be output at a particular time, which is determined by the processor(s) 912 based on the ECG signal and/or the impedance signal.

The processor(s) 912 is operably connected to a charging circuit 922 and a discharge circuit 924. In various implementations, the charging circuit 922 includes a power source 926, one or more charging switches 928, and one or more capacitors 930. The power source 926 includes, for instance, a battery. The processor(s) 912 initiates a defibrillation shock by causing the power source 926 to charge at least one capacitor among the capacitor(s) 930. For example, the processor(s) 912 activates at least one of the charging switch(es) 928 in the charging circuit 922 to complete a first circuit connecting the power source 926 and the capacitor to be charged. Then, the processor(s) 912 causes the discharge circuit 924 to discharge energy stored in the charged capacitor across a pair of defibrillation electrodes 934, which are in contact with the individual 908. For example, the processor(s) 912 deactivates the charging switch(es) 928 completing the first circuit between the capacitor(s) 930 and the power source 926, and activates one or more discharge switches 932 completing a second circuit connecting the charged capacitor 930 and at least a portion of the individual 908 disposed between defibrillation electrodes 934.

The energy is discharged from the defibrillation electrodes 934 in the form of a defibrillation shock. For example, the defibrillation electrodes 934 are connected to the skin of the individual 908 and located at positions on different sides of the heart of the individual 908, such that the defibrillation shock is applied across the heart of the individual 908. The defibrillation shock, in various examples, depolarizes a significant number of heart cells in a short amount of time. The defibrillation shock, for example, interrupts the propagation of the shockable rhythm (e.g., VF or V-Tach) through the heart. In some examples, the defibrillation shock is 200 J or greater with a duration of about 0.015 seconds. In some cases, the defibrillation shock has a multiphasic (e.g., biphasic) waveform. The discharge switch(es) 932 are controlled by the processor(s) 912, for example. In various implementations, the defibrillation electrodes 934 are connected to defibrillation leads 936. The defibrillation leads 936 are connected to a defibrillation port 938, in implementations. According to various examples, the defibrillation leads 936 are removable from the defibrillation port 938. For example, the defibrillation leads 936 are plugged into the defibrillation port 938.

In various implementations, the processor(s) 912 is operably connected to one or more transceivers 940 that transmit and/or receive data over one or more communication networks 942. For example, the transceiver(s) 940 includes a network interface card (NIC), a network adapter, a local area network (LAN) adapter, or a physical, virtual, or logical address to connect to the various external devices and/or systems. In various examples, the transceiver(s) 940 includes any sort of wireless transceivers capable of engaging in wireless communication (e.g., radio frequency (RF) communication). For example, the communication network(s) 942 includes one or more wireless networks that include a 3rd Generation Partnership Project (3GPP) network, such as a Long Term Evolution (LTE) radio access network (RAN) (e.g., over one or more LTE bands), a New Radio (NR) RAN (e.g., over one or more NR bands), or a combination thereof. In some cases, the transceiver(s) 940 includes other wireless modems, such as a modem for engaging in WI-FI®, WIGIG®, WIMAX®, BLUETOOTH®, or infrared communication over the communication network(s) 942.

The defibrillator 900 is configured to transmit and/or receive data (e.g., ECG data, impedance data, data indicative of one or more detected heart rhythms of the individual 908, data indicative of one or more defibrillation shocks administered to the individual 908, etc.) with one or more external devices 944 via the communication network(s) 942. The external devices 944 include, for instance, mobile devices (e.g., mobile phones, smart watches, etc.), Internet of Things (IoT) devices, medical devices, computers (e.g., laptop devices, servers, etc.), or any other type of computing device configured to communicate over the communication network(s) 942. In some examples, the external device(s) 944 is located remotely from the defibrillator 900, such as at a remote clinical environment (e.g., a hospital). According to various implementations, the processor(s) 912 causes the transceiver(s) 940 to transmit data to the external device(s) 944. In some cases, the transceiver(s) 940 receives data from the external device(s) 944 and the transceiver(s) 940 provide the received data to the processor(s) 912 for further analysis.

In various implementations, the memory 914 includes a recorder 925 which, when executed by the processor(s) 912, causes the processor(s) 912 to generate or update an electronic record. In some cases, the electronic record includes data indicative of at least one physiological parameter detected by the external defibrillator 900, such as the ECG. In some examples, the electronic record includes data indicative of at least one treatment administered by the external defibrillator 900 to the individual 906, such as an energy level of an electrical shock administered by the defibrillation electrodes 934. In various examples, the recorder 925 causes the processor(s) 912 to identify and communicate with an additional medical device, which may be one of the external devices 944. For example, the recorder 925 may cause the external defibrillator 900 to operate as a tracking device described herein.

In various implementations, the external defibrillator 900 also includes a housing 946 that at least partially encloses other elements of the external defibrillator 900. For example, the housing 946 encloses the detection circuit 910, the processor(s) 912, the memory 914, the charging circuit 922, the transceiver(s) 940, or any combination thereof. In some cases, the input device(s) 918 and output device(s) 920 extend from an interior space at least partially surrounded by the housing 946 through a wall of the housing 946. In various examples, the housing 946 acts as a barrier to moisture, electrical interference, and/or dust, thereby protecting various components in the external defibrillator 900 from damage.

In some implementations, the external defibrillator 900 is an automated external defibrillator (AED) operated by an untrained user (e.g., a bystander, layperson, etc.) and can be operated in an automatic mode. In automatic mode, the processor(s) 912 automatically identifies a rhythm in the ECG signal, makes a decision whether to administer a defibrillation shock, charges the capacitor(s) 930, discharges the capacitor(s) 930, or any combination thereof. In some cases, the processor(s) 912 controls the output device(s) 920 to output (e.g., display) a simplified user interface to the untrained user. For example, the processor(s) 912 refrains from causing the output device(s) 920 to display a waveform of the ECG signal and/or the impedance signal to the untrained user, in order to simplify operation of the external defibrillator 900.

In some examples, the external defibrillator 900 is a monitor-defibrillator utilized by a trained user (e.g., a clinician, an emergency responder, etc.) and can be operated in a manual mode or the automatic mode. When the external defibrillator 900 operates in manual mode, the processor(s) 912 cause the output device(s) 920 to display a variety of information that may be relevant to the trained user, such as waveforms indicating the ECG data and/or impedance data, notifications about detected heart rhythms, and the like.

Figure 10:
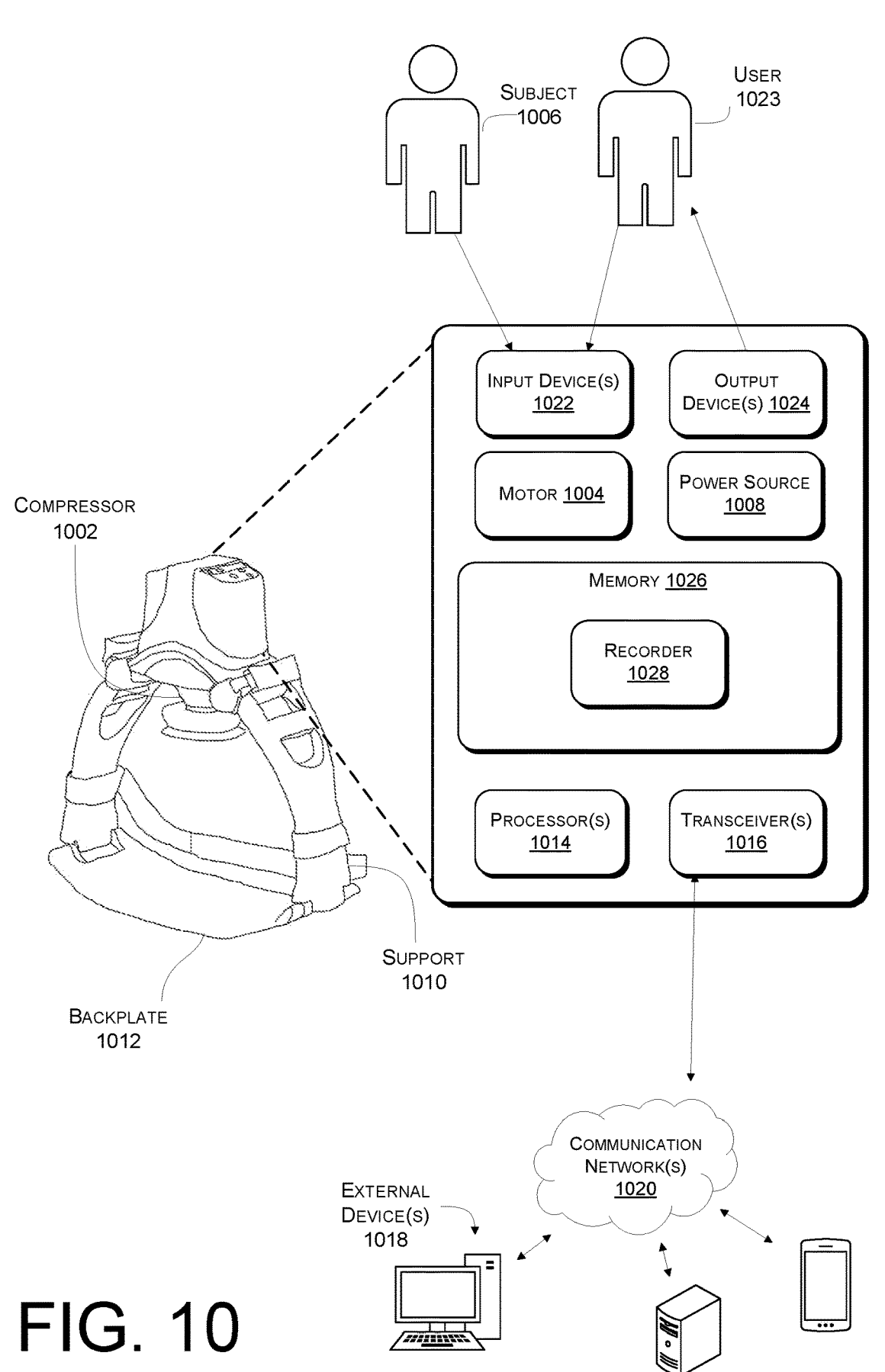
FIG. 10 illustrates a chest compression device configured to perform various functions described herein.

FIG. 10 illustrates a chest compression device 1000 configured to perform various functions described herein. For example, the chest compression device 1000 is the medical device 106 or subsequent medical device 122 described in FIG. 1.

In various implementations, the chest compression device 1000 includes a compressor 1002 that is operatively coupled to a motor 1004. The compressor 1002 physically administers a force to the chest of a subject 1006 that compresses the chest of the subject 1006. In some examples, the compressor 1002 includes at least one piston that periodically moves between two positions (e.g., a compressed position and a release position) at a compression frequency. For example, when the piston is positioned on the chest of the subject 1006, the piston compresses the chest when the piston is moved into the compressed position. A suction cup may be positioned on a tip of the piston, such that the suction cup contacts the chest of the subject 1006 during operation. In various cases, the compressor 1002 includes a band that periodically tightens to a first tension and loosens to a second tension at a compression frequency. For instance, when the band is disposed around the chest of the subject 1006, the band compresses the chest when the band tightens.

The motor 1004 is configured to convert electrical energy stored in a power source 1008 into mechanical energy that moves and/or tightens the compressor 1002, thereby causing the compressor 1002 to administer the force to the chest of the subject 1006. In various implementations, the power source 1008 is portable. For instance, the power source 1008 includes at least one rechargeable (e.g., lithium-ion) battery. In some cases, the power source 1008 supplies electrical energy to one or more elements of the chest compression device 1000 described herein.

In various cases, the chest compression device 1000 includes a support 1010 that is physically coupled to the compressor 1002, such that the compressor 1002 maintains a position relative to the subject 1006 during operation. In some implementations, the support 1010 is physically coupled to a backplate 1012, cot, or other external structure with a fixed position relative to the subject 1006. According to some cases, the support 1010 is physically coupled to a portion of the subject 1006, such as wrists of the subject 1006.

The operation of the chest compression device 1000 may be controlled by at least one processor 1014. In various implementations, the motor 1004 is communicatively coupled to the processor(s) 1014. Specifically, the processor(s) 1014 is configured to output a control signal to the motor 1004 that causes the motor 1004 to actuate the compressor 1002. For instance, the motor 1004 causes the compressor 1002 to administer the compressions to the subject 1006 based on the control signal. In some cases, the control signal indicates one or more treatment parameters of the compressions. Examples of treatment parameters include a frequency, timing, depth, force, position, velocity, and acceleration of the compressor 1002 administering the compressions. According to various cases, the control signal causes the motor 1004 to cease compressions.

In various implementations, the chest compression device 1000 includes at least one transceiver 1016 configured to communicate with at least one external device 1018 over one or more communication networks 1020. Any communication network described herein can be included in the communication network(s) 1020 illustrated in FIG. 10. The external device(s) 1018, for example, includes at least one of a monitor-defibrillator, an AED, an ECMO device, a ventilation device, a patient monitor, a mobile phone, a server, or a computing device. In some implementations, the transceiver(s) 1016 is configured to communicate with the external device(s) 1018 by transmitting and/or receiving signals wirelessly. For example, the transceiver(s) 1016 includes a NIC, a network adapter, a LAN adapter, or a physical, virtual, or logical address to connect to the various external devices and/or systems. In various examples, the transceiver(s) 1016 includes any sort of wireless transceivers capable of engaging in wireless communication (e.g., RF communication). For example, the communication network(s) 1020 includes one or more wireless networks that include a 3GPP network, such as an LTE RAN (e.g., over one or more LTE bands), an NR RAN (e.g., over one or more NR bands), or a combination thereof. In some cases, the transceiver(s) 1016 includes other wireless modems, such as a modem for engaging in WI-FI®, WIGIG®, WIMAX®, BLUETOOTH®, or infrared communication over the communication network(s) 1020. The signals, in various cases, encode data in the form of data packets, datagrams, or the like. In some cases, the signals are transmitted as compressions are being administered by the chest compression device 1000 (e.g., for real-time feedback by the external device(s) 1018), after compressions are administered by the chest compression device 1000 (e.g., for post-event review at the external device 1018), or a combination thereof.

In various cases, the processor(s) 1014 generates the control signal based on data encoded in the signals received from the external device(s) 1018. For instance, the signals include an instruction to initiate the compressions, and the processor(s) 1014 instructs the motor 1004 to begin actuating the compressor 1002 in accordance with the signals.

In some cases, the chest compression device 1000 includes at least one input device 1022. In various examples, the input device(s) 1022 is configured to receive an input signal from a user 1023, who may be a rescuer treating the subject 1006. Examples of the input device(s) 1022 include, for instance, at a keypad, a cursor control, a touch-sensitive display, a voice input device (e.g., a microphone), a haptic feedback device (e.g., a gyroscope), or any combination thereof. In various implementations, the processor(s) 1014 generate the control signal based on the input signal. For instance, the processor(s) 1014 generate the control signal to adjust a frequency of the compressions based on the chest compression device 1000 detecting a selection by the user 1023 of a user interface element displayed on a touchscreen or detecting the user 1023 pressing a button integrated with an external housing of the chest compression device 1000. In some cases, the input device(s) 1022 include a camera or microphone configured to capture an image or sound of the subject 1006, the user 1023, or another medical device. The input device(s) 122, in some cases, include additional sensors configured to detect other types of physiological parameters of the subject 1006.

According to some examples, the input device(s) 1022 include one or more sensors. The sensor(s), for example, is configured to detect a physiological parameter of the subject 1006. In some implementations, the sensor(s) is configured to detect a state parameter of the chest compression device 1000, such as a position of the compressor 1002 with respect to the subject 1006 or the backplate 1012, a force administered by the compressor 1002 on the subject 1006, a force administered onto the backplate 1012 by the body of the subject 1006 during a compression, or the like. According to some implementations, the signals transmitted by the transceiver(s) 1016 indicate the physiological parameter(s) and/or the state parameter(s).

The chest compression device 1000 further includes at least one output device 1024, in various implementations. Examples of the output device(s) 1024 include, for instance, least one of a display (e.g., a projector, an LED screen, etc.), a speaker, a haptic output device, a printer, or any combination thereof. In some implementations, the output device(s) 1024 include a screen configured to display various parameters detected by and/or reported to the chest compression device 1000, a charge level of the power source 1008, a timer indicating a time since compressions were initiated or paused, and other relevant information.

The chest compression device 1000 further includes memory 1026. In various implementations, the memory 1026 is volatile (such as random access memory (RAM)), non-volatile (such as read only memory (ROM), flash memory, etc.) or some combination of the two. The memory 1026 stores instructions that, when executed by the processor(s) 1014, causes the processor(s) 1014 to perform various operations. In various examples, the memory 1026 stores methods, threads, processes, applications, objects, modules, any other sort of executable instruction, or a combination thereof. In some cases, the memory 1026 stores files, databases, or a combination thereof. In some examples, the memory 1026 includes, but is not limited to, RAM, ROM, EEPROM, flash memory, or any other memory technology. In some examples, the memory 1026 includes one or more of CD-ROMs, DVDs, CAM, or other optical storage, magnetic cassettes, magnetic tape, magnetic disk storage or other magnetic storage devices, or any other medium which can be used to store the desired information. In various cases, the memory 1026 stores instructions, programs, threads, objects, data, or any combination thereof, that cause the processor(s) 1014 to perform various functions. In various cases, the memory 1026 stores one or more parameters that are detected by the chest compression device 1000 and/or reported to the chest compression device 1000.

In implementations of the present disclosure, the memory 1026 also stores instructions for executing a recorder 1028. In various implementations, the recorder 1028, when executed by the processor(s) 1014, causes the processor(s) 1014 to perform operations that enable the chest compression device 1000 to update or generate an electronic record (e.g., as a tracking device described herein).

EXAMPLE CLAUSES

1. A tracking device, including: a camera configured to capture an image of a medical device that is monitoring or treating a patient; a transceiver; and a processor configured to: determine an identifier of the medical device by analyzing the image; identify a physiological parameter of the patient, the physiological parameter being detected by a different device than the medical device; generate an electronic record of the patient, the electronic record including the identifier and the physiological parameter; and cause the transceiver to transmit the electronic record to a server.

2. The tracking device of clause 1, wherein the processor is configured to determine the identifier of the medical device by: detecting an identification number displayed on the medical device and depicted in the image; detecting a QR code displayed on the medical device; or identifying a visual characteristic of the medical device and depicted in the image and determining that the visual characteristic matches a predetermined visual characteristic associated with the medical device.

3. The tracking device of clause 1 or 2, wherein the identifier includes an identification number of the medical device, a manufacturer of the medical device, a model of the medical device, or a portion of the image.

4. A device, including: a processor configured to: identify a signal corresponding to a medical device associated with a patient; determine an identifier of the medical device by analyzing the signal; identify a physiological parameter of the patient; generate an electronic record of the patient, the electronic record including the identifier and the physiological parameter; and output the electronic record.

5. The device of clause 4, further including a sensor configured to detect the signal.

6. The device of clause 5, wherein the sensor includes a camera, and wherein the signal includes an image of the medical device or an image of a tag attached to a housing of the medical device.

7 The device of clause 5 or 6, wherein the sensor includes a microphone and the signal includes a sound output by the medical device.

8. The device of clause 7, wherein the microphone is configured to detect an audio prompt output by the medical device, wherein the processor is configured to determine the identifier of the medical device by: identifying a manufacturer of the medical device by analyzing the audio prompt, the identifier including the manufacturer of the medical device.

9. The device of any one of clauses 5 to 8, the sensor being a first sensor, the device further including: a second sensor configured to detect the physiological parameter.

10. The device of any one of clauses 4 to 9, wherein the signal includes an electromagnetic signal emitted by a transceiver of the medical device or emitted by a tag attached to a housing of the medical device.

11. The device of any one of clauses 4 to 10, wherein the electronic record further indicates an identifier of a rescuer operating the device, or an identifier of the patient.

12. The device of any one of clauses 4 to 11, further including: a location service circuit configured to identify a location of the device, wherein the electronic record further indicates the location of the device.

13. The device of any one of clauses 4 to 12, further including: a transceiver configured to receive an indication of the physiological parameter from an external device.

14. The device of any one of clauses 4 to 13, further including: a transceiver configured to transmit the electronic record to an external device.

15. A method, including: determining an identifier of the medical device by analyzing a signal corresponding to a medical device associated with a patient; identifying a physiological parameter of the patient; generating an electronic record of the patient, the electronic record including the identifier and the physiological parameter; and outputting the electronic record.

16. The method of clause 15, further including: detecting, by a sensor, the signal corresponding to the medical device associated with the patient.

17. The method of clause 15 or 16, wherein detecting the signal corresponding to the medical device associated with the patient includes capturing an image of a display of the medical device or an image of a tag attached to a housing of the medical device.

18. The method of any one of clauses 15 to 17, wherein the signal includes an electromagnetic signal emitted by a transceiver of the medical device or a tag attached to a housing of the medical device.

19. The method of any one of clauses 15 to 18, wherein the signal includes a sound output by the medical device.

20. The method of any one of clauses 15 to 19, wherein identifying the physiological parameter of the patient includes detecting the physiological parameter of the patient.

21. The method of any one of clauses 15 to 20, wherein the electronic record further includes a time at which the sensor detects the signal, an identifier of a rescuer operating the device, demographic information about the patient, a condition of the patient, or a location of the patient.

22. The method of any one of clauses 15 to 21, wherein identifying the physiological parameter of the patient includes receiving an indication of the physiological parameter from an external device.

23. The method of any one of clauses 15 to 22, wherein outputting the electronic record includes transmitting the electronic record to an external device or storing the electronic record in a database.

24. A monitor-defibrillator, including: a first sensor configured to detect a signal from a tag affixed to an automated external defibrillator (AED) that has administered a treatment to a patient; a detection circuit configured to detect a first electrocardiogram (ECG) of the patient; a transceiver; and a processor configured to: determine pairing information of the AED by analyzing the signal; generate a pairing request using the pairing information; cause the transceiver to transmit the pairing request to the AED; in response to causing the transceiver to transmit the pairing request to the AED, determine that the transceiver has received a response indicating a second ECG of the patient detected by the AED and a treatment parameter characterizing the treatment; generate an electronic record including the first ECG, the second ECG, and the treatment parameter; and cause the transceiver to transmit the electronic record to an external device.

25. The monitor-defibrillator of clause 24, wherein the signal includes a radio frequency (RF) signal.

26. The monitor-defibrillator of clause 24 or 25, wherein the monitor-defibrillator further includes: a location service circuit configured to determine a location of the monitor-defibrillator, wherein the electronic record further indicates the location of the monitor-defibrillator and information about the patient.

27. A device, including: a sensor configured to detect a first signal from a medical device; a transceiver; and a processor configured to: identifying connection information by analyzing the first signal; causing the transceiver to establish a communication session with the medical device using the connection information; in response to causing the transceiver to establish the communication session with the medical device, determine that the transceiver has received a second signal indicating a physiological parameter; generate an electronic record including the physiological parameter and information about the medical device; and output the electronic record.

28. The device of clause 27, wherein the sensor is configured to detect the first signal from a tag affixed to the medical device.

29. The device of clause 27 or 28, wherein the sensor includes a camera configured to capture an image of the medical device, and wherein the processor is configured to determine the connection information by identifying a QR code indicated in the image.

30. The device of any one of clauses 27 to 29, wherein the sensor includes a microphone and the signal includes a sound output by the medical device.

31. The device of any one of clauses 27 to 30, wherein the processor is configured to identify the connection information by analyzing the first signal by: determining an identifier of the medical device by analyzing the first signal; identifying an entry of a database including the identifier; and reading the connection information from the entry.

32. The device of any one of clauses 27 to 31, wherein the connection information includes an identifier of the medical device or an encryption key.

33. The device of any one of clauses 27 to 32, wherein the processor is further configured to: determine that the transceiver has received a third signal indicating a treatment parameter characterizing a treatment administered by the medical device to the patient, wherein the electronic record further includes the treatment parameter.

34. The device of any one of clauses 27 to 33, further including: a location service circuit configured to determine a location of the device, wherein the electronic record further indicates the location of the device.

35. The device of any one of clauses 27 to 34, the sensor being a first sensor, the physiological parameter being a first physiological parameter of a patient, the device further including: a second sensor configured to detect a second physiological parameter of the patient, wherein the patient record further indicates the second physiological parameter.

36. The device of any one of clauses 27 to 35, wherein the device includes another medical device, a mobile device, a wearable device, an autonomous vehicle, or a robot.

37. A method including: detecting a signal from a medical device; determining pairing information of the medical device by analyzing the signal; generating a pairing request using the pairing information; transmitting the pairing request to the medical device; in response to transmitting the pairing request to the medical device, receiving a response indicating a physiological parameter; generating an electronic record including the physiological parameter; and outputting the electronic record.

38. The method of clause 37, wherein detecting the signal from the medical device includes detecting the signal from a tag affixed to the medical device.

39. The method of clause 37 or 38, wherein determining the pairing information of the medical device by analyzing the signal includes: determining an identifier of the medical device by analyzing the signal; identifying an entry of a database including the identifier; and reading the pairing information from the entry.

40. The method of any one of clauses 37 to 39, wherein the pairing information includes an identifier of the medical device or an encryption key.

41. The method of any one of clauses 37 to 40, wherein the physiological parameter includes an electrocardiogram (ECG), a heart rate, a pulse rate, a blood pressure, or a ventilation parameter.

42. The method of any one of clauses 37 to 41, the response being a first response, further including: receiving a second response indicating a treatment parameter characterizing a treatment administered by the medical device to the patient, wherein the electronic record further includes the treatment parameter.

43. The method of any one of clauses 37 to 42, further including: determining a location of the medical device, wherein the electronic record further indicates the location of the medical device.

44. The method of any one of clauses 37 to 43, the physiological parameter being a first physiological parameter of a patient, the method further including: detecting a second physiological parameter of the patient, wherein the patient record further indicates the second physiological parameter.

45. An emergency support device, including: a camera configured to capture a first image of a patient and a second image of a medical device associated with the patient; a movement component configured to move the emergency support device in an emergency scene including the patient, the medical device, and a rescuer; and a processor configured to: determine a feature of the patient by analyzing the first image; determine an identifier of the medical device by analyzing the second image of the medical device; generate an electronic record including the feature of the patient and the identifier of the medical device; and output the electronic record.

46. The emergency support device of clause 45, wherein the camera is configured to capture a video of the emergency scene, the video including the first image and the second image.

47. The emergency support device of clause 46, wherein the electronic record includes a portion of the video including the first image.

48. The emergency support device of clause 46 or 47, wherein the processor is further configured to: identify a position of the patient in the emergency scene by analyzing the video; and cause the movement component to move the emergency support device from a first location to a second location corresponding to the position of the patient, and wherein the camera is configured to capture the first image in response to the emergency support device moving to the second location.

49. The emergency support device of any one of clauses 46 to 48, wherein the processor is further configured to:

identify a position of an anomaly in the emergency scene by analyzing the video; and cause the movement component to move the emergency support device from a first location to a second location corresponding to the position of the anomaly, and wherein the camera is configured to capture the first image in response to the emergency support device moving to the second location.

50. The emergency support device of any one of clauses 45 to 49, further including: a temperature sensor configured to detect a heatmap of the emergency scene, wherein the processor is configured to: identify a position of the patient in the emergency scene by analyzing the heatmap; and cause the movement component to move the emergency support device from a first location to a second location corresponding to the position of the patient.

51. The emergency support device of any one of clauses 45 to 50, wherein the movement component includes a propeller, a robotic leg, or a wheel.

52. The emergency support device of any one of clauses 45 to 51, further including: a light source configured to emit light into the emergency scene.

53. The emergency support device of any one of clauses 45 to 52, further including: an output device configured to output an alert associated with the patient to the rescuer.

54. The emergency support device of any one of clauses 45 to 53, further including: a location service circuit configured to detect a location of the emergency support device.

The features disclosed in the foregoing description, or the following claims, or the accompanying drawings, expressed in their specific forms or in terms of a means for performing the disclosed function, or a method or process for attaining the disclosed result, as appropriate, may separately, or in any combination of such features, be used for realizing implementations of the disclosure in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities, properties, conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain implementations are described herein, including the best mode known to the inventors for carrying out implementations of the disclosure. Of course, variations on these described implementations will become apparent to those of ordinary skill in the art upon reading the foregoing description. The inventors expect skilled artisans to employ such variations as appropriate, and the inventors intend for implementations to be practiced otherwise than specifically described herein. Accordingly, the scope of this disclosure includes all modifications and equivalents of the subject matter recited in the claims appended hereto as permitted by applicable law. Moreover, any combination of the above-described elements in all possible variations thereof is encompassed by implementations of the disclosure unless otherwise indicated herein or otherwise clearly contradicted by context.

34

What is claimed is:

1. A tracking device, comprising:
a camera configured to capture an image of a medical device associated with a patient;
a microphone configured to detect an audible signal from the medical device;
a transceiver; and
a processor configured to:
determine, by inputting the image into a convolutional neural network (CNN) that is trained to identify medical devices, transforming the image into a feature map associated with the medical device, and analyzing a spectral feature of the audible signal and matching the spectral feature to a predetermined tone uniquely associated with a model of the medical device, an identifier of the medical device;
determine, by analyzing the audible signal, that the medical device has administered an electrical shock to the patient;
identify a physiological parameter of the patient, the physiological parameter being detected by a different device than the medical device;
generate an electronic record of the patient, the electronic record comprising the identifier, an indication of the electrical shock, and the physiological parameter; and
cause the transceiver to transmit the electronic record to a server;
wherein the tracking device is configured to operate independently without receiving a communication from the medical device.

2. The tracking device of claim 1, wherein the identifier comprises an identification number of the medical device, a manufacturer of the medical device, a model of the medical device, or a portion of the image.

3. The tracking device of claim 1, wherein the processor is configured to correlate the identifier determined from the image with the electrical shock determined from the audible signal to verify a source of the electrical shock within the electronic record.

4. A device, comprising:
a sensor configured to detect a visual signal or an audible signal from a medical device associated with a patient; and
a processor configured to:
determine, by analyzing the visual signal or the audible signal using a first machine learning (ML) model, an identifier of the medical device;
determine, by analyzing the audible signal or the visual signal using a second ML model, an identifier of the patient;
identify a physiological parameter of the patient;
generate an electronic record of the patient, the electronic record comprising the identifier, the identifier of the patient, and the physiological parameter; and
output the electronic record,
wherein determining the identifier of the medical device comprises analyzing a spectral feature of the audible signal and matching the spectral feature to a predetermined tone uniquely associated with a model of the medical device; and
wherein the device is configured to operate independently without receiving a communication from the medical device.

5. The device of claim 4, wherein the sensor comprises a camera, wherein the visual signal comprises an image of the medical device, and wherein the ML model comprises a CNN.

6. The device of claim 4, wherein the sensor comprises a microphone configured to detect the audible signal from the medical device.

7. The device of claim 6, wherein the microphone is configured to detect an audio prompt output by the medical device, the audio prompt comprising an audible instruction for operating the medical device, the audio prompt being uniquely associated with a model of the medical device, wherein the processor is configured to determine the identifier of the medical device by:

identifying the model of the medical device by analyzing the audio prompt, the identifier comprising the model of the medical device.

8. The device of claim 4, wherein the processor is configured to identify the physiological parameter of the patient by analyzing the visual signal or the audible signal.

9. The device of claim 4, the medical device being a first medical device, the device being a second medical device further comprising:

a treatment component configured to administer an additional treatment to the patient, wherein the electronic record further comprises an indication of the additional treatment.

10. A method, comprising:

determining, by a processor of a device, by analyzing a visual signal and an audible signal detected by a sensor of a medical device using a machine learning (ML) model, an identifier of the medical device associated with a patient;

determining, by the processor, that a first treatment has been administered to the patient by the medical device by analyzing the visual signal or the audible signal, identify, by the processor, a treatment parameter associated with the first treatment and a physiological parameter of the patient;

determining, by the processor, that the first treatment temporarily resolved a condition of the patient;

in response to determining that the first treatment temporarily resolved the condition of the patient, causing a treatment component of the device to administer, to the patient, a second treatment associated with the treatment parameter;

generating, by the processor, an electronic record of the patient, the electronic record comprising the identifier, the treatment parameter, and the physiological parameter; and outputting the electronic record;

wherein determining the identifier of the medical device associated with the patient comprises analyzing a spectral feature of the audible signal and matching the spectral feature to a predetermined tone uniquely associated with a model of the medical device.

11. The method of claim 10, wherein detecting the visual signal comprises capturing an image of a display of the medical device.

12. The method of claim 10, wherein identifying the physiological parameter of the patient comprises:

detecting the physiological parameter of the patient; or receiving an indication of the physiological parameter from an external device.

13. The method of claim 10, wherein the electronic record further comprises a time at which the sensor detects the visual signal and the audible signal, an identifier of a rescuer operating the medical device, demographic information about the patient, a condition of the patient, or a location of the patient.

14. The method of claim 10, wherein outputting the electronic record comprises transmitting the electronic record to an external device or storing the electronic record in a database.

15. The method of claim 10, wherein the first treatment comprises a first electrical shock and the second treatment comprises a second electrical shock.

* * * * *